(12) United States Patent
Stafford et al.

(10) Patent No.: US 8,647,620 B2
(45) Date of Patent: Feb. 11, 2014

(54) CHIMERIC FACTOR VII MOLECULES

(75) Inventors: Darrel W. Stafford, Carrboro, NC (US); Dengmin Feng, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 125 days.

(21) Appl. No.: 12/823,382

(22) Filed: Jun. 25, 2010

(65) Prior Publication Data

US 2010/0330059 A1    Dec. 30, 2010

Related U.S. Application Data

(60) Provisional application No. 61/220,278, filed on Jun. 25, 2009.

(51) Int. Cl.
  *A61K 38/00* (2006.01)
  *C12N 9/96* (2006.01)
  *C12N 15/86* (2006.01)
  *C12N 7/00* (2006.01)
  *C12N 15/52* (2006.01)
  *C07K 14/75* (2006.01)
  *G01N 33/535* (2006.01)

(52) U.S. Cl.
  USPC ...... 424/94.3; 514/14.9; 435/369; 435/320.1; 435/188; 536/23.2; 424/94.64

(58) Field of Classification Search
  None
  See application file for complete search history.

(56) References Cited

U.S. PATENT DOCUMENTS

| | | | |
|---|---|---|---|
| 2003/0044908 | A1 | 3/2003 | Persson |
| 2006/0234935 | A1* | 10/2006 | Blajchman et al. ............. 514/12 |
| 2007/0065440 | A1 | 3/2007 | Tomlinson et al. |
| 2009/0093410 | A1 | 4/2009 | Uttenthal |
| 2009/0098103 | A1* | 4/2009 | Madison et al. ........... 424/94.64 |
| 2010/0330059 | A1 | 12/2010 | Stafford et al. |
| 2012/0064075 | A1 | 3/2012 | Stafford et al. |

FOREIGN PATENT DOCUMENTS

| | | |
|---|---|---|
| WO | WO 2007/149406 A2 | 12/2007 |
| WO | WO 2008/127702 A2 | 10/2008 |
| WO | WO 2008/145139 A1 | 12/2008 |
| WO | WO 2009/126307 A2 | 10/2009 |

OTHER PUBLICATIONS

Melton et al., Location of the platelet binding site in zymogen coagulaiton factor IX, Blood Coagulation and Fibrinolysis 2001, 12: 237-243.*

Kenet et al., A new approach to treatment of bleeding episodes in young hemophilia patients: a single bolus megadose of recombinant activated factor VII (NovoSeven), Journal of Thrmobosis and Haemostasis, 1: 450-455.*

Ahmad et al. "High-Affinity, Specific Factor IXa Binding to Platelets is Mediated in Part by Residues 3-11" Biochemistry 1994, 33, 12048.*

Melton et al. "Location of the platelet binding site in zymogen coagulation factor IX" Blood Coagulaiton and Fibrinolysis 2001, 237-243.*

(Continued)

*Primary Examiner* — Blaine Lankford, Jr.
*Assistant Examiner* — Lauren K Van Buren
(74) *Attorney, Agent, or Firm* — Myers Bigel Sibley & Sajovec, PA

(57) ABSTRACT

The present invention relates to chimeric Factor VII polypeptides and methods of using the same.

7 Claims, 7 Drawing Sheets

(56) References Cited

OTHER PUBLICATIONS

Aljamali et al. "Long-Term Expression of Murine Activated Factor VII is Safe, but Elevated Levels Cause Premature Mortality" *The Journal of Clinical Investigation* 118(5):1825-1834 (2008).
Buyue et al. "The Heparin-Binding Exosite of Factor IXa is a Critical Regulator of Plasma Thrombin Generation and Venous Thrombosis" *Blood* 112(8):3234-3241 (2008).
Ellison et al. "Adsorption of Vitamin K-Dependent Blood Coagulation Proteins to Spread Phospholipid Monolayers as Determined from Combined Measurements of the Surface Pressure and Surface Protein Concentration" *Biochemistry* 37:7997-8003 (1998).
de Grouchy et al. "Regional Mapping of Clotting Factors VII and X to 13q34. Expression of Factor VII Through Chromosome 8" *Hum Genet* 66:230-233 (1984).
Fischer et al. "The interaction of Factor VIIa with Rehydrated, Lyophilized Platelets" *Platelets* 19(3):182-191 (2008).
Gui et al. Circulating and Binding Characteristics of Wild-Type Factor IX and Certain Gla Domain Mutants in vivo 100(1):153-158 (2002).
Gui et al. "Abnormal Hemostasis in a Knock-in Mouse Carrying a Variant of Factor IX with Impaired Binding to Collagen Type IV" *Journal of Thrombosis and Haemostasis* 7:1843-1851 2009).
Hedner et al. "Use of Human Factor VIIa in the Treatment of Two Hemophilia A Patients with High-Titer Inhibitors" *J. Clin. Invest.* 71:1836-1841 (1983).
Gawande "Casualties of War—Military Care for the Wounded from Iraq and Afghanistan" *N Engl J Med* 351(24):2471-2475 (2004).
Hoffman et al. "Factors IXa and Xa Play Distinct Roles in Tissue Factor-Dependent Initiation of Coagulation" *Blood* 86(5):1794-1801 (1995).
Hoffman et al. "Tissue Factor Around Dermal Vessels has Bound Factor VII in the Absence of Injury" *Journal of Thrombosis and Haemostasis* 5:1403-1408 (2007).
Margaritis et al. "Successful Treatment of Canine Hemophilia by Continuous Expression of Canine FVIIa" *Blood* 113(16):3682-3689 (2009).
Margaritis et al. "Novel Therapeutic Approach for Hemophilia Using Gene Delivery of an Engineered Secreted Activated Factor VII" *The Journal of Clinical Investigation* 113(7):1025-1031 (2004).
Monroe et al. "Platelet Activity of High-Dose Factor VIIa is Independent of Tissue Factor" *British Journal of Haematology* 99:542-547 (1997).
Monroe et al. "Transmission of a Procoagulant Signal from Tissue Factor-Bearing Cells to Platelets" *Blood Coagulation and Fibrinolysis* 7:459-464 (1996).
Moss et al. "Evaluation of the Safety and Pharmacokinetics of a Fast-Acting Recombinant FVIIa Analogue, NN1731, in Healthy Male Subjects" *Journal of Thrombosis and Haemostasis* 7:299-305 (2008).
Nelsestuen et al. "Elevated Function of Blood Clotting Factor VIIa Mutants that Have Enhanced Affinity for Membranes" *The Journal of E3iological Chemistry* 276(43):39825-39831 (2001).
O'Hara et al. "Nucleotide Sequence of the Gene Coding for Human Factor VII, a Vitamin K-Dependent Protein Participating in Blood Coagulation" *Proc. Natl. Acad. Sci.* 84:5158-5162 (1987).
Perkins et al. "Early Versus Late Recombinant Factor VIIa in Combat Trauma Patients Requiring Massive Transfusion" *J Trauma* 62(5):1095-1101 (2007).
Stennicke et al. "Generation and Biochemical Characterization of GlycoPEGylated Factor VIIa Derivatives" *Thromb Haemost* 100:920-928 (2008).
Sunnerhagen et al. "Structure of the $Ca^{2+}$-Free GLA Domain Sheds Light on Membrane Binding of Blood Coagulation Proteins" *Nature Structural Biology* 2(6):504-509 (1995).
Sunnerhagen et al. "The Relative Orientation of Gla and EGF Domains in Coagulation Factor X is Altered by $Ca^{2+}$-Binding to the First EGF Domain. A Combined NMR-Small Angle X-Ray Scattering Study" *Biochemistry* 35:11547-11559 (1996).
van 't Veer et al. "Regulation of Tissue Factor Initiated Thrombin Generation by the Stoichiometric Inhibitors Tissue Factor Pathway Inhibitor, Antithrombin-III, and Heparin Cofactor-II" *The Journal of Biological Chemistry* 272(7):4367-4377 (1997).
Wu et al. "Optimization of Self-Complementary AAV Vectors for Liver-Directed Expression Results in Sustained Correction of Hemophilia B at Low Vector Dose" *Molecular Therapy* 16(2):280-289 (2008).
Yoshitake et al. "Nucleotide Sequence of the Gene for Human Factor IX (Antihemophilic Factor B)" *Biochemistry* 24:3736-3750 (1985).
PCT International Preliminary Report on Patentability mailed Jan. 12, 2012 for PCT International Application No. PCT/US2010/039934, filed Jun. 25, 2010.
Cain et al. "Assembly of the Warfarin-Sensitive Vitamin K 2,3-Epoxide Reductase Enzyme Complex in the Endoplasmic Reticulum Membrane" *The Journal of Biological Chemistry* 272(46):29068-29075 (1997).
Cheung et al. "The Binding of Human Factor IX to Endothelial Cells is Mediated by Residues 3-11" *The Journal of Biological Chemistry* 267(29):20529-20531 (1992).
Cheung et al. "Identification of the Endothelial Cell Binding Site for Factor IX" *PNAS USA* 93:11069-11073 (1996).
Chenung et al. "Localization of a Calcium-Dependent Epitope to the Amino Terminal Region of the Gla Domain of Human Factor IX" *Thrombosis Research* 81(1):65-73 (1996).
Cheung et al. "Localization of a Metal-Dependent Epitope to the Amino Terminal Residues 33-40 of Human Factor IX" *Thrombosis Research* 80(5):419-427 (1995).
Lee and Fasco. "Metabolism of Vitamin K and Vitamin K 2,3-Epoxide via Interaction with a Common Disulfide" *Biochemistry* 23:2246-2252 (1984).
Melton et al. "Location of the Platelet Binding Site in Zymogen Coagulation Factor IX" *Blood Coagulation and Fibrinolysis* 12:237-243 (2001).
Mukharji and Silverman. "Purification of a Vitamin K Epoxide Reductase That Catalyzes Conversion of Vitamin K 2,3-Epoxide to 3-Hydroxy-2-Methyl-3-Phytyl-2,3-Dihydronaphoquinone" *PNAS USA* 82:2713-2717 1985.
Siegfried. "Purification and Properties of a Factor from Rat Liver Cytosol Which Stimulates Vitamin K Epoxide Reductase" *Archives of Biochemistry and Biophysics* 223(1):129-139 (1983).
Ahmad et al. "High-Affinity, Specific Factor IXa Binding to Platelets Is Mediated in Part by Residues 3-11" *Biochemistry* 33:12048-12055 (1994).
Camire et al. "Enhanced γ-Carboxylation of Recombinant Factor X Using a Chimeric Construct Containing the Prothrombin Propeptide" *Biochemistry* 39:14322-14329 (2000).
Chang et al. "The Roles of Factor VII's Structural Domains in Tissue Factor Binding" *Biochemistry* 34:12227-12232 (1995).
Chang et al. "Replacing the First Epidermal Growth Factor-Like Domain of Factor IX with That of Factor VII Enhances Activity In Vitro and in Canine Hemophilia B" *J. Clin. Invest.* 100(4):886-892 (Aug. 1997).
Cheung et al. "The Binding of Human Factor IX to Endothelial Cells is Mediated by Residues 3-11*" *The Journal of Biological Chemistry* 267(29):20529-31 (1992).
Cheung et al. "Identification of the Endothelial Cell Binding Site for Factor IX" *Proc. Natl. Acad. Sci.* 93:11068-11073 (Oct. 1996).
Hamaguchi et al. "Mutations in the Catalytic Domain of Factor IX That Are Related to the Subclass Hemophilia Bm" *Biochemistry* 32:6324-6329 (1993).
International Search Report and Written Opinion for PCT/US2010/039934, mailed Sep. 10, 2010.
Jin et al. "Factor VIIa's First Epidermal Growth Factor-Like Domain's Role in Catalytic Activity" *Biochemistry* 38:1185-1192 (1999).
Jin et al. "Four Loops of the Catalytic Domain of Factor VIIa Mediate the Effect of the First EGF-Like Domain Substitution on Factor VIIa Catalytic Activity" *J. Mol. Biol.* 307:1503-1517 (2001).
Jin et al. "Residues Y179 and H101 of a Hydrophobic Patch of Factor VII Are Involved in Activation by Factor Xa" *Biochemistry* 40:11405-11410 (2001).

(56) References Cited

OTHER PUBLICATIONS

Lin et al. "Expression and Characterization of Human Factor IX and Factor IX-Factor X Chimeras in Mouse C127 Cells*" *The Journal of Biological Chemistry* 265(1):144-150 (Jan. 1990).

Melton et al. "Location of the Platelet Binding Site in Zymogen Coagulation Factor IX" *Blood Coagulation and Fibrinolysis* 12(4):237-243 (2001).

Ndonwi et al. "Substitution of the Gla Domain in Factor X with That of Protein C Impairs Its Interaction with Factor VIIa/Tissue Factor" *The Journal of Biological Chemistry* 282(21):15632-15644 (May 2007).

O'Brien et al. "Glycosaminoglycans Bind Factor Xa in a $Ca^{2+}$-Dependent Fashion and Modulate Its Catalytic Activity" *Biochemistry* 42:13091-13098 (2003).

Perera et al. "Modeling Zymogen Protein C" *Biophysical Journal* 79:2925-2943 (Dec. 2000).

Stanley et al. "The Propeptides of the Vitamin K-dependent Proteins Possess Different Affinities for the Vitamin K-dependent Carboxylase*" *The Journal of Biological Chemistry* 74(24):16940-16944 (Jun. 1999).

Toomey et al. "Localization of the Human Tissue Factor Recognition Determinant of Human Factor VIIa*"*The Journal of Biological Chemistry* 266(29):19198-19202 (Oct. 1991).

Toomey et al. "The Endothelial Cell Binding Determinant of Human Factor IX Resides in the γ-Carboxyglutamic Acid Domain" *Biochemistry* 31:1806-1808 (1992).

Ware et al. "Genetic Defect Responsible for the Dysfunction Protein: Factor $IX_{Long\ Beach}$" *Blood* 72(2):820-822 (Aug. 1988).

Wolberg et al. "Factor IX Activation by Factor XIa Proceeds without Release of a Free Intermediate" *Biochemistry* 36:4074-4079 (1997).

International Search Report and Written Opinion issued for International Application No. PCT/US2012/035642; Date of Mailing: Jul. 12, 2012; 16 Pages.

Bennett et al. "DNA Binding to Human Leukocytes" *J. Clin. Invest.* 76:2182-2190 (1985).

Dickinson et al. "Identification of Surface Residues Mediating Tissue Factor Binding and Catalytic Function of the Serine Protease Factor VIIa" *PNAS* 93:14379-14384 (1996).

Edelstein et al, "Gene Therapy Clinical Trials Worldwide to 2007-an Update" *J. Gene. Med.* 9:833-842 (2007).

Erhardtsen "Pharmacokinetics of Recombinant Activated Factor VII (rFVIIa)" *Semin. Thromb. Hemost.* 26(4):385-391 (2000).

Rao et al. "Binding of Factor VIIa to Tissue Factor Permits Rapid Antithrombin III/Heparin Inhibition of Factor VIIa" *Blood* 81(10):2600-2607 (1993).

Rapaport "Inhibition of Factor VII/Tissue Factor Induce Blood Coagulation: With Particular Emphasis Upon a Factor Xa Dependent Inhibitory Mechanism" *Blood* 73(2):359365 (1989).

Stryer *Biochemistry* pp. 248-250 (1988).

\* cited by examiner

MQRVNMIMAESPGLITICLLGYLLSAECTVFLDHENANKILNRPKRYNSGKLE
EFVQGNLERECMEEKCSFEEAAREVFENTERTTEFWKQYVDGDQCESNPCL
NGGSCKDDINSYECWCPFGFEGKNCELHKDDQLICVNENGGCEQYCSDHT
GTKRSCRCHEGYSLLADGVSCTPTVEYPCGKIPILEKRNASKPQGRIVGGKV
CPKGECPWQVLLLVNGAQLCGGTLINTIWVVSAAHCFDKIKNVVRNLIAVLGE
HDLSEHDGDEQSRRVAQVIIPSTYVPGTTNHDIALLRLHQPVVLTDHVVPLCL
PERTFSERTLAFVRFSLVSGWGQLLDRGATALELMVLNVPRLMTQDCLQQS
RKVGDSPNITEYMFCAGYSDGSKDSCKGDSSGGPHATHYRGTWYLTGIVSW
GQGCATVGHFGVYTRVSQYIEWLQKLMRSEPRPGVLLRAPFP

FIG. 6

MQRVNMIMAESPGLITICLLGYLLSAECTVFLDHENANKILNRPKRANSLLEETKQ
GNLERECIEELCNKEEAREVFENDPETDYFYPKYLVDGDQCESNPCLNGGSCK
DDINSYECWCPFGFEGKNCELHKDDQLICVNENGGCEQYCSDHTGTKRSCRCH
EGYSLLADGVSCTPTVEYPCGKIPILEKRNASKPQGRIVGGKVCPKGECPWQVL
LVNGAQLCGGTLINTIWVVSAAHCFDKIKNWRNLIAVLGEHDLSEHDGDEQSRR
VAQVIIPSTYVPGTTNHDIALLRLHQPVVLTDHVVPLCLPERTFSERTLAFVRFSLV
SGWGQLLDRGATALELMVLNVPRLMTQDCLQQSRKVGDSPNITEYMFCAGYSD
GSKDSCKGDSGGPHATHYRGTWYLTGIVSWGQGCATVGHFGVYTRVSQYIEW
LQKLMRSEPRPGVLLRAPFP

FIG. 7

SEQUENCE LISTING

<160> NUMBER OF SEQ ID NOS: 21

<210> SEQ ID NO 1
<211> LENGTH: 453
<212> TYPE: PRT
<213> ORGANISM: Artificial
<220> FEATURE:
<223> OTHER INFORMATION: Chimeric Factor VII protein sequence

<400> SEQUENCE: 1

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

```
Ser Gly Lys Leu Glu Glu Phe Val Gln Gly Asn Leu Glu Arg Glu Cys
    50                  55                  60
Met Glu Glu Lys Cys Ser Phe Glu Glu Ala Arg Glu Val Phe Glu Asn
65                  70                  75                  80
Thr Glu Arg Thr Thr Glu Phe Trp Lys Gln Tyr Val Asp Gly Asp Gln
                85                  90                  95
Cys Glu Ser Asn Pro Cys Leu Asn Gly Gly Ser Cys Lys Asp Asp Ile
                100                 105                 110
Asn Ser Tyr Glu Cys Trp Cys Pro Phe Gly Phe Glu Gly Lys Asn Cys
            115                 120                 125
Glu Leu His Lys Asp Asp Gln Leu Ile Cys Val Asn Glu Asn Gly Gly
    130                 135                 140
Cys Glu Gln Tyr Cys Ser Asp His Thr Gly Thr Lys Arg Ser Cys Arg
145                 150                 155                 160
Cys His Glu Gly Tyr Ser Leu Leu Ala Asp Gly Val Ser Cys Thr Pro
                165                 170                 175
Thr Val Glu Tyr Pro Cys Gly Lys Ile Pro Ile Leu Glu Lys Arg Asn
                180                 185                 190
Ala Ser Lys Pro Gln Gly Arg Ile Val Gly Gly Lys Val Cys Pro Lys
            195                 200                 205
Gly Glu Cys Pro Trp Gln Val Leu Leu Leu Val Asn Gly Ala Gln Leu
    210                 215                 220
Cys Gly Gly Thr Leu Ile Asn Thr Ile Trp Val Val Ser Ala Ala His
225                 230                 235                 240
Cys Phe Asp Lys Ile Lys Asn Trp Arg Asn Leu Ile Ala Val Leu Gly
                245                 250                 255
Glu His Asp Leu Ser Glu His Asp Gly Asp Glu Gln Ser Arg Arg Val
                260                 265                 270
Ala Gln Val Ile Ile Pro Ser Thr Tyr Val Pro Gly Thr Thr Asn His
            275                 280                 285
Asp Ile Ala Leu Leu Arg Leu His Gln Pro Val Val Leu Thr Asp His
    290                 295                 300
Val Val Pro Leu Cys Leu Pro Glu Arg Thr Phe Ser Glu Arg Thr Leu
305                 310                 315                 320
Ala Phe Val Arg Phe Ser Leu Val Ser Gly Trp Gly Gln Leu Leu Asp
                325                 330                 335
Arg Gly Ala Thr Ala Leu Glu Leu Met Val Leu Asn Val Pro Arg Leu
            340                 345                 350
Met Thr Gln Asp Cys Leu Gln Gln Ser Arg Lys Val Gly Asp Ser Pro
    355                 360                 365
Asn Ile Thr Glu Tyr Met Phe Cys Ala Gly Tyr Ser Asp Gly Ser Lys
    370                 375                 380
Asp Ser Cys Lys Gly Asp Ser Gly Gly Pro His Ala Thr His Tyr Arg
385                 390                 395                 400
Gly Thr Trp Tyr Leu Thr Gly Ile Val Ser Trp Gly Gln Gly Cys Ala
                405                 410                 415
Thr Val Gly His Phe Gly Val Tyr Thr Arg Val Ser Gln Tyr Ile Glu
                420                 425                 430
Trp Leu Gln Lys Leu Met Arg Ser Glu Pro Arg Pro Gly Val Leu Leu
            435                 440                 445
Arg Ala Pro Phe Pro
    450
```

```
<210> SEQ ID NO 2
<211> LENGTH: 453
<212> TYPE: PRT
<213> ORGANISM: Artificial
<220> FEATURE:
<223> OTHER INFORMATION: Chimeric Factor VII protein sequence

<400> SEQUENCE: 2

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Ala Asn
            35                  40                  45

Ser Leu Leu Glu Glu Thr Lys Gln Gly Asn Leu Glu Arg Glu Cys Ile
        50                  55                  60

Glu Glu Leu Cys Asn Lys Glu Ala Arg Glu Val Phe Glu Asn Asp
65                  70                  75                  80

Pro Glu Thr Asp Tyr Phe Tyr Pro Lys Tyr Leu Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu His Lys Asp Asp Gln Leu Ile Cys Val Asn Glu Asn Gly Gly
    130                 135                 140

Cys Glu Gln Tyr Cys Ser Asp His Thr Gly Thr Lys Arg Ser Cys Arg
145                 150                 155                 160

Cys His Glu Gly Tyr Ser Leu Leu Ala Asp Gly Val Ser Cys Thr Pro
                165                 170                 175

Thr Val Glu Tyr Pro Cys Gly Lys Ile Pro Ile Leu Glu Lys Arg Asn
            180                 185                 190

Ala Ser Lys Pro Gln Gly Arg Ile Val Gly Gly Lys Val Cys Pro Lys
        195                 200                 205

Gly Glu Cys Pro Trp Gln Val Leu Leu Leu Val Asn Gly Ala Gln Leu
    210                 215                 220

Cys Gly Gly Thr Leu Ile Asn Thr Ile Trp Val Val Ser Ala Ala His
225                 230                 235                 240

Cys Phe Asp Lys Ile Lys Asn Trp Arg Asn Leu Ile Ala Val Leu Gly
                245                 250                 255

Glu His Asp Leu Ser Glu His Asp Gly Asp Glu Gln Ser Arg Arg Val
            260                 265                 270

Ala Gln Val Ile Ile Pro Ser Thr Tyr Val Pro Gly Thr Thr Asn His
        275                 280                 285

Asp Ile Ala Leu Leu Arg Leu His Gln Pro Val Val Leu Thr Asp His
    290                 295                 300

Val Val Pro Leu Cys Leu Pro Glu Arg Thr Phe Ser Glu Arg Thr Leu
305                 310                 315                 320

Ala Phe Val Arg Phe Ser Leu Val Ser Gly Trp Gly Gln Leu Leu Asp
                325                 330                 335

Arg Gly Ala Thr Ala Leu Glu Leu Met Val Leu Asn Val Pro Arg Leu
            340                 345                 350

Met Thr Gln Asp Cys Leu Gln Gln Ser Arg Lys Val Gly Asp Ser Pro
        355                 360                 365

Asn Ile Thr Glu Tyr Met Phe Cys Ala Gly Tyr Ser Asp Gly Ser Lys
    370                 375                 380
```

```
Asp Ser Cys Lys Gly Asp Ser Gly Pro His Ala Thr His Tyr Arg
385                 390                 395                 400

Gly Thr Trp Tyr Leu Thr Gly Ile Val Ser Trp Gln Gly Cys Ala
            405                 410                 415

Thr Val Gly His Phe Gly Val Tyr Thr Arg Val Ser Gln Tyr Ile Glu
            420                 425                 430

Trp Leu Gln Lys Leu Met Arg Ser Glu Pro Arg Pro Gly Val Leu Leu
        435                 440                 445

Arg Ala Pro Phe Pro
    450

<210> SEQ ID NO 3
<211> LENGTH: 446
<212> TYPE: PRT
<213> ORGANISM: Mus musculus

<400> SEQUENCE: 3

Met Val Pro Gln Ala His Gly Leu Leu Leu Leu Cys Phe Leu Leu Gln
1               5                   10                  15

Leu Gln Gly Pro Leu Gly Thr Ala Val Phe Ile Thr Gln Glu Glu Ala
            20                  25                  30

His Gly Val Leu His Arg Gln Arg Arg Ala Asn Ser Leu Leu Glu Glu
        35                  40                  45

Leu Trp Pro Gly Ser Leu Glu Arg Glu Cys Asn Glu Glu Gln Cys Ser
50                  55                  60

Phe Glu Glu Ala Arg Glu Ile Phe Lys Ser Pro Glu Arg Thr Lys Gln
65                  70                  75                  80

Phe Trp Ile Val Tyr Ser Asp Gly Asp Gln Cys Ala Ser Asn Pro Cys
                85                  90                  95

Gln Asn Gly Gly Thr Cys Gln Asp His Leu Lys Ser Tyr Val Cys Phe
            100                 105                 110

Cys Leu Leu Asp Phe Glu Gly Arg Asn Cys Glu Lys Ser Lys Asn Glu
        115                 120                 125

Gln Leu Ile Cys Ala Asn Glu Asn Gly Asp Cys Asp Gln Tyr Cys Arg
    130                 135                 140

Asp His Val Gly Thr Lys Arg Thr Cys Ser Cys His Glu Asp Tyr Thr
145                 150                 155                 160

Leu Gln Pro Asp Glu Val Ser Cys Lys Pro Lys Val Glu Tyr Pro Cys
                165                 170                 175

Gly Arg Ile Pro Val Val Glu Lys Arg Asn Ser Ser Arg Gln Gly
            180                 185                 190

Arg Ile Val Gly Gly Asn Val Cys Pro Lys Gly Glu Cys Pro Trp Gln
        195                 200                 205

Ala Val Leu Lys Ile Asn Gly Leu Leu Leu Cys Gly Ala Val Leu Leu
    210                 215                 220

Asp Ala Arg Trp Ile Val Thr Ala Ala His Cys Phe Asp Asn Ile Arg
225                 230                 235                 240

Tyr Trp Gly Asn Ile Thr Val Val Met Gly Glu His Asp Phe Ser Glu
                245                 250                 255

Lys Asp Gly Asp Glu Gln Val Arg Arg Val Thr Gln Val Ile Met Pro
            260                 265                 270

Asp Lys Tyr Ile Arg Gly Lys Ile Asn His Asp Ile Ala Leu Leu Arg
        275                 280                 285

Leu His Arg Pro Val Thr Phe Asp Tyr Val Val Pro Leu Cys Leu
    290                 295                 300
```

```
Pro Glu Lys Ser Phe Ser Glu Asn Thr Leu Ala Arg Ile Arg Phe Ser
305                 310                 315                 320

Arg Val Ser Gly Trp Gly Gln Leu Leu Asp Arg Gly Ala Thr Ala Leu
            325                 330                 335

Glu Leu Met Ser Ile Glu Val Pro Arg Leu Met Thr Gln Asp Cys Leu
        340                 345                 350

Glu His Ala Lys His Ser Ser Asn Thr Pro Lys Ile Thr Glu Asn Met
    355                 360                 365

Phe Cys Ala Gly Tyr Met Asp Gly Thr Lys Asp Ala Cys Lys Gly Asp
370                 375                 380

Ser Gly Gly Pro His Ala Thr His Tyr His Gly Thr Trp Tyr Leu Thr
385                 390                 395                 400

Gly Val Val Ser Trp Gly Glu Gly Cys Ala Ala Ile Gly His Ile Gly
            405                 410                 415

Val Tyr Thr Arg Val Ser Gln Tyr Ile Asp Trp Leu Val Arg His Met
        420                 425                 430

Asp Ser Lys Leu Gln Val Gly Val Phe Arg Leu Pro Leu Leu
    435                 440                 445

<210> SEQ ID NO 4
<211> LENGTH: 452
<212> TYPE: PRT
<213> ORGANISM: Artificial
<220> FEATURE:
<223> OTHER INFORMATION: Wild-type mouse Factor VII with RKRRKR
      secretion signal sequence

<400> SEQUENCE: 4

Met Val Pro Gln Ala His Gly Leu Leu Leu Leu Cys Phe Leu Leu Gln
1               5                   10                  15

Leu Gln Gly Pro Leu Gly Thr Ala Val Phe Ile Thr Gln Glu Glu Ala
            20                  25                  30

His Gly Val Leu His Arg Gln Arg Ala Asn Ser Leu Leu Glu Glu
        35                  40                  45

Leu Trp Pro Gly Ser Leu Glu Arg Glu Cys Asn Glu Glu Gln Cys Ser
50                  55                  60

Phe Glu Glu Ala Arg Glu Ile Phe Lys Ser Pro Glu Arg Thr Lys Gln
65                  70                  75                  80

Phe Trp Ile Val Tyr Ser Asp Gly Asp Gln Cys Ala Ser Asn Pro Cys
            85                  90                  95

Gln Asn Gly Gly Thr Cys Gln Asp His Leu Lys Ser Tyr Val Cys Phe
        100                 105                 110

Cys Leu Leu Asp Phe Glu Gly Arg Asn Cys Glu Lys Ser Lys Asn Glu
    115                 120                 125

Gln Leu Ile Cys Ala Asn Glu Asn Gly Asp Cys Asp Gln Tyr Cys Arg
130                 135                 140

Asp His Val Gly Thr Lys Arg Thr Cys Ser Cys His Glu Asp Tyr Thr
145                 150                 155                 160

Leu Gln Pro Asp Glu Val Ser Cys Lys Pro Lys Val Glu Tyr Pro Cys
            165                 170                 175

Gly Arg Ile Pro Val Val Glu Lys Arg Asn Ser Ser Arg Gln Gly
        180                 185                 190

Arg Arg Lys Arg Arg Lys Arg Ile Val Gly Gly Asn Val Cys Pro Lys
    195                 200                 205

Gly Glu Cys Pro Trp Gln Ala Val Leu Lys Ile Asn Gly Leu Leu Leu
210                 215                 220
```

```
Cys Gly Ala Val Leu Leu Asp Ala Arg Trp Ile Val Thr Ala Ala His
225                 230                 235                 240

Cys Phe Asp Asn Ile Arg Tyr Trp Gly Asn Ile Thr Val Val Met Gly
            245                 250                 255

Glu His Asp Phe Ser Glu Lys Asp Gly Asp Glu Gln Val Arg Arg Val
                260                 265                 270

Thr Gln Val Ile Met Pro Asp Lys Tyr Ile Arg Gly Lys Ile Asn His
            275                 280                 285

Asp Ile Ala Leu Leu Arg Leu His Arg Pro Val Thr Phe Thr Asp Tyr
        290                 295                 300

Val Val Pro Leu Cys Leu Pro Glu Lys Ser Phe Ser Glu Asn Thr Leu
305                 310                 315                 320

Ala Arg Ile Arg Phe Ser Arg Val Ser Gly Trp Gly Gln Leu Leu Asp
                325                 330                 335

Arg Gly Ala Thr Ala Leu Glu Leu Met Ser Ile Glu Val Pro Arg Leu
                340                 345                 350

Met Thr Gln Asp Cys Leu Glu His Ala Lys His Ser Ser Asn Thr Pro
            355                 360                 365

Lys Ile Thr Glu Asn Met Phe Cys Ala Gly Tyr Met Asp Gly Thr Lys
        370                 375                 380

Asp Ala Cys Lys Gly Asp Ser Gly Gly Pro His Ala Thr His Tyr His
385                 390                 395                 400

Gly Thr Trp Tyr Leu Thr Gly Val Val Ser Trp Gly Glu Gly Cys Ala
                405                 410                 415

Ala Ile Gly His Ile Gly Val Tyr Thr Arg Val Ser Gln Tyr Ile Asp
                420                 425                 430

Trp Leu Val Arg His Met Asp Ser Lys Leu Gln Val Gly Val Phe Arg
            435                 440                 445

Leu Pro Leu Leu
    450

<210> SEQ ID NO 5
<211> LENGTH: 458
<212> TYPE: PRT
<213> ORGANISM: Artificial
<220> FEATURE:
<223> OTHER INFORMATION: Chimeric Factor VII protein sequence

<400> SEQUENCE: 5

Met Lys His Leu Asn Thr Val Met Ala Glu Ser Pro Ala Leu Ile Thr
1               5                   10                  15

Ile Phe Leu Leu Gly Tyr Leu Leu Ser Thr Glu Cys Ala Val Phe Leu
            20                  25                  30

Asp Arg Glu Asn Ala Thr Lys Ile Leu Thr Arg Pro Lys Arg Tyr Asn
        35                  40                  45

Ser Gly Lys Leu Glu Glu Phe Val Arg Gly Asn Leu Glu Arg Glu Cys
    50                  55                  60

Ile Glu Glu Arg Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Ile Cys Lys Asp Asp Ile
            100                 105                 110

Ser Ser Tyr Glu Cys Trp Cys Gln Val Gly Phe Glu Gly Arg Asn Cys
        115                 120                 125
```

Glu Phe Ser Lys Asn Glu Gln Leu Ile Cys Ala Asn Glu Asn Gly Asp
            130                 135                 140

Cys Asp Gln Tyr Cys Arg Asp His Val Gly Thr Lys Arg Thr Cys Ser
145                 150                 155                 160

Cys His Glu Asp Tyr Thr Leu Gln Pro Asp Glu Val Ser Cys Lys Pro
                165                 170                 175

Lys Val Glu Tyr Pro Cys Gly Arg Ile Pro Val Val Glu Lys Arg Asn
                180                 185                 190

Ser Ser Ser Arg Gln Gly Arg Arg Lys Arg Lys Arg Ile Val Gly
            195                 200                 205

Gly Asn Val Cys Pro Lys Gly Glu Cys Pro Trp Gln Ala Val Leu Lys
210                 215                 220

Ile Asn Gly Leu Leu Cys Gly Ala Val Leu Asp Ala Arg Trp
225                 230                 235                 240

Ile Val Thr Ala Ala His Cys Phe Asp Asn Ile Arg Tyr Trp Gly Asn
                245                 250                 255

Ile Thr Val Val Met Gly Glu His Asp Phe Ser Glu Lys Asp Gly Asp
                260                 265                 270

Glu Gln Val Arg Arg Val Thr Gln Val Ile Met Pro Asp Lys Tyr Ile
            275                 280                 285

Arg Gly Lys Ile Asn His Asp Ile Ala Leu Leu Arg Leu His Arg Pro
290                 295                 300

Val Thr Phe Thr Asp Tyr Val Val Pro Leu Cys Leu Pro Glu Lys Ser
305                 310                 315                 320

Phe Ser Glu Asn Thr Leu Ala Arg Ile Arg Phe Ser Arg Val Ser Gly
                325                 330                 335

Trp Gly Gln Leu Leu Asp Arg Gly Ala Thr Ala Leu Glu Leu Met Ser
            340                 345                 350

Ile Glu Val Pro Arg Leu Met Thr Gln Asp Cys Leu Glu His Ala Lys
            355                 360                 365

His Ser Ser Asn Thr Pro Lys Ile Thr Glu Asn Met Phe Cys Ala Gly
            370                 375                 380

Tyr Met Asp Gly Thr Lys Asp Ala Cys Lys Gly Asp Ser Gly Gly Pro
385                 390                 395                 400

His Ala Thr His Tyr His Gly Thr Trp Tyr Leu Thr Gly Val Val Ser
                405                 410                 415

Trp Gly Glu Gly Cys Ala Ala Ile Gly His Ile Gly Val Tyr Thr Arg
                420                 425                 430

Val Ser Gln Tyr Ile Asp Trp Leu Val Arg His Met Asp Ser Lys Leu
            435                 440                 445

Gln Val Gly Val Phe Arg Leu Pro Leu Leu
        450                 455

<210> SEQ ID NO 6
<211> LENGTH: 457
<212> TYPE: PRT
<213> ORGANISM: Artificial
<220> FEATURE:
<223> OTHER INFORMATION: Chimeric Factor VII protein sequence

<400> SEQUENCE: 6

Met Lys His Leu Asn Thr Val Met Ala Glu Ser Pro Ala Leu Ile Thr
1               5                   10                  15

Ile Phe Leu Leu Gly Tyr Leu Leu Ser Thr Glu Cys Ala Val Phe Leu
            20                  25                  30

Asp Arg Glu Asn Ala Thr Lys Ile Leu Thr Arg Pro Lys Arg Ala Asn

```
                    35                  40                  45
Thr Leu Phe Glu Glu Thr Met Lys Gly Asn Leu Glu Arg Glu Cys Ile
 50                  55                  60

Glu Glu Leu Cys Asn Lys Glu Ala Arg Glu Val Phe Glu Asn Asn
 65                  70                  75                  80

Pro Glu Thr Asp Tyr Phe Tyr Lys Gln Tyr Val Asp Gly Asp Gln Cys
                     85                  90                  95

Glu Ser Asn Pro Cys Leu Asn Gly Gly Ile Cys Lys Asp Ile Ser
                100                 105                 110

Ser Tyr Glu Cys Trp Cys Gln Val Gly Phe Glu Gly Arg Asn Cys Glu
                115                 120                 125

Phe Ser Lys Asn Glu Gln Leu Ile Cys Ala Asn Glu Asn Gly Asp Cys
                130                 135                 140

Asp Gln Tyr Cys Arg Asp His Val Gly Thr Lys Arg Thr Cys Ser Cys
145                 150                 155                 160

His Glu Asp Tyr Thr Leu Gln Pro Asp Glu Val Ser Cys Lys Pro Lys
                    165                 170                 175

Val Glu Tyr Pro Cys Gly Arg Ile Pro Val Val Glu Lys Arg Asn Ser
                180                 185                 190

Ser Ser Arg Gln Gly Arg Arg Lys Arg Lys Arg Ile Val Gly Gly
                195                 200                 205

Asn Val Cys Pro Lys Gly Glu Cys Pro Trp Gln Ala Val Leu Lys Ile
210                 215                 220

Asn Gly Leu Leu Leu Cys Gly Ala Val Leu Leu Asp Ala Arg Trp Ile
225                 230                 235                 240

Val Thr Ala Ala His Cys Phe Asp Asn Ile Arg Tyr Trp Gly Asn Ile
                    245                 250                 255

Thr Val Val Met Gly Glu His Asp Phe Ser Glu Lys Asp Gly Asp Glu
                260                 265                 270

Gln Val Arg Arg Val Thr Gln Val Ile Met Pro Asp Lys Tyr Ile Arg
                275                 280                 285

Gly Lys Ile Asn His Asp Ile Ala Leu Leu Arg Leu His Arg Pro Val
290                 295                 300

Thr Phe Thr Asp Tyr Val Val Pro Leu Cys Leu Pro Glu Lys Ser Phe
305                 310                 315                 320

Ser Glu Asn Thr Leu Ala Arg Ile Arg Phe Ser Arg Val Ser Gly Trp
                325                 330                 335

Gly Gln Leu Leu Asp Arg Gly Ala Thr Ala Leu Glu Leu Met Ser Ile
                340                 345                 350

Glu Val Pro Arg Leu Met Thr Gln Asp Cys Leu Glu His Ala Lys His
                355                 360                 365

Ser Ser Asn Thr Pro Lys Ile Thr Glu Asn Met Phe Cys Ala Gly Tyr
                370                 375                 380

Met Asp Gly Thr Lys Asp Ala Cys Lys Gly Asp Ser Gly Gly Pro His
385                 390                 395                 400

Ala Thr His Tyr His Gly Thr Trp Tyr Leu Thr Gly Val Val Ser Trp
                    405                 410                 415

Gly Glu Gly Cys Ala Ala Ile Gly His Ile Gly Val Tyr Thr Arg Val
                420                 425                 430

Ser Gln Tyr Ile Asp Trp Leu Val Arg His Met Asp Ser Lys Leu Gln
                435                 440                 445

Val Gly Val Phe Arg Leu Pro Leu Leu
                450                 455
```

<210> SEQ ID NO 7
<211> LENGTH: 37
<212> TYPE: DNA
<213> ORGANISM: Artificial
<220> FEATURE:
<223> OTHER INFORMATION: PCR primer

<400> SEQUENCE: 7
tgaggatccc caccatggtt ccacaggcgc atgggct                              37

<210> SEQ ID NO 8
<211> LENGTH: 37
<212> TYPE: DNA
<213> ORGANISM: Artificial
<220> FEATURE:
<223> OTHER INFORMATION: PCR primer

<400> SEQUENCE: 8
ttccccagca tgcctacagt agtgggagtc ggaaaac                              37

<210> SEQ ID NO 9
<211> LENGTH: 46
<212> TYPE: DNA
<213> ORGANISM: Artificial
<220> FEATURE:
<223> OTHER INFORMATION: PCR primer

<400> SEQUENCE: 9
acaatgcgtt ttcgccgctt acggcggcct tggcggctgc tggagt                    46

<210> SEQ ID NO 10
<211> LENGTH: 46
<212> TYPE: DNA
<213> ORGANISM: Artificial
<220> FEATURE:
<223> OTHER INFORMATION: PCR primer

<400> SEQUENCE: 10
gccgccgtaa gcggcgaaaa cgcattgtgg gaggcaacgt gtgccc                    46

<210> SEQ ID NO 11
<211> LENGTH: 40
<212> TYPE: DNA
<213> ORGANISM: Artificial
<220> FEATURE:
<223> OTHER INFORMATION: PCR primer

<400> SEQUENCE: 11
aggcctgaag atctccacca tgaagcacct gaacaccgtc                           40

<210> SEQ ID NO 12
<211> LENGTH: 47
<212> TYPE: DNA
<213> ORGANISM: Artificial
<220> FEATURE:
<223> OTHER INFORMATION: PCR primer

<400> SEQUENCE: 12
gatcagctgc tcattcttgc ttttttcaca gttccttcct tcaaatc                   47

<210> SEQ ID NO 13
<211> LENGTH: 47
<212> TYPE: DNA
<213> ORGANISM: Artificial
<220> FEATURE:
<223> OTHER INFORMATION: PCR primer -continued

<400> SEQUENCE: 13
gatttgaagg aaggaactgt gaaaaaagca agaatgagca gctgatc                47

<210> SEQ ID NO 14
<211> LENGTH: 48
<212> TYPE: DNA
<213> ORGANISM: Artificial
<220> FEATURE:
<223> OTHER INFORMATION: PCR primer

<400> SEQUENCE: 14
gtttcttcga acaaggtatt tgctctcttt ggacgggtaa gaattttg               48

<210> SEQ ID NO 15
<211> LENGTH: 48
<212> TYPE: DNA
<213> ORGANISM: Artificial
<220> FEATURE:
<223> OTHER INFORMATION: PCR primer

<400> SEQUENCE: 15
caaaattctt acccgtccaa agagagcaaa taccttgttc gaagaaac               48

<210> SEQ ID NO 16
<211> LENGTH: 46
<212> TYPE: DNA
<213> ORGANISM: Artificial
<220> FEATURE:
<223> OTHER INFORMATION: PCR primer

<400> SEQUENCE: 16
gatctccatc aacatactgc ttataaaaat aatccgtctc gggatt                 46

<210> SEQ ID NO 17
<211> LENGTH: 46
<212> TYPE: DNA
<213> ORGANISM: Artificial
<220> FEATURE:
<223> OTHER INFORMATION: PCR primer

<400> SEQUENCE: 17
aatcccgaga cggattattt ttataagcag tatgttgatg gagatc                 46

<210> SEQ ID NO 18
<211> LENGTH: 466
<212> TYPE: PRT
<213> ORGANISM: Homo sapiens

<400> SEQUENCE: 18

Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Ala Asn Ala Phe
    50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
        115                 120                 125

Ile Cys Phe Cys Leu Pro Ala Phe Glu Gly Arg Asn Cys Glu Thr His
130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
            165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
            195                 200                 205

Pro Gln Gly Arg Ile Val Gly Gly Lys Val Cys Pro Lys Gly Glu Cys
    210                 215                 220

Pro Trp Gln Val Leu Leu Leu Val Asn Gly Ala Gln Leu Cys Gly Gly
225                 230                 235                 240

Thr Leu Ile Asn Thr Ile Trp Val Val Ser Ala Ala His Cys Phe Asp
            245                 250                 255

Lys Ile Lys Asn Trp Arg Asn Leu Ile Ala Val Leu Gly Glu His Asp
            260                 265                 270

Leu Ser Glu His Asp Gly Asp Glu Gln Ser Arg Arg Val Ala Gln Val
            275                 280                 285

Ile Ile Pro Ser Thr Tyr Val Pro Gly Thr Thr Asn His Asp Ile Ala
    290                 295                 300

Leu Leu Arg Leu His Gln Pro Val Val Leu Thr Asp His Val Val Pro
305                 310                 315                 320

Leu Cys Leu Pro Glu Arg Thr Phe Ser Glu Arg Thr Leu Ala Phe Val
            325                 330                 335

Arg Phe Ser Leu Val Ser Gly Trp Gly Gln Leu Leu Asp Arg Gly Ala
            340                 345                 350

Thr Ala Leu Glu Leu Met Val Leu Asn Val Pro Arg Leu Met Thr Gln
            355                 360                 365

Asp Cys Leu Gln Gln Ser Arg Lys Val Gly Asp Ser Pro Asn Ile Thr
    370                 375                 380

Glu Tyr Met Phe Cys Ala Gly Tyr Ser Asp Gly Ser Lys Asp Ser Cys
385                 390                 395                 400

Lys Gly Asp Ser Gly Gly Pro His Ala Thr His Tyr Arg Gly Thr Trp
            405                 410                 415

Tyr Leu Thr Gly Ile Val Ser Trp Gly Gln Gly Cys Ala Thr Val Gly
            420                 425                 430

His Phe Gly Val Tyr Thr Arg Val Ser Gln Tyr Ile Glu Trp Leu Gln
            435                 440                 445

Lys Leu Met Arg Ser Glu Pro Arg Pro Gly Val Leu Leu Arg Ala Pro
    450                 455                 460

Phe Pro
465

<210> SEQ ID NO 19
<211> LENGTH: 461
<212> TYPE: PRT
<213> ORGANISM: Homo sapiens

<400> SEQUENCE: 19

Met Gln Arg Val Asn Met Ile Met Ala Glu Ser Pro Ser Leu Ile Thr
1               5                   10                  15

-continued

Ile Cys Leu Leu Gly Tyr Leu Leu Ser Ala Glu Cys Thr Val Phe Leu
            20                  25                  30
Asp His Glu Asn Ala Asn Lys Ile Leu Asn Arg Pro Lys Arg Tyr Asn
                35                  40                  45
Ser Gly Lys Leu Glu Glu Phe Val Gln Gly Asn Leu Glu Arg Glu Cys
50                  55                  60
Met Glu Lys Cys Ser Phe Glu Glu Pro Arg Glu Val Phe Glu Asn
65                  70                  75                  80
Thr Glu Lys Thr Thr Glu Phe Trp Lys Gln Tyr Val Asp Gly Asp Gln
                85                  90                  95
Cys Glu Ser Asn Pro Cys Leu Asn Gly Gly Ser Cys Lys Asp Asp Ile
                100                 105                 110
Asn Ser Tyr Glu Cys Trp Cys Pro Phe Gly Phe Glu Gly Lys Asn Cys
                115                 120                 125
Glu Leu Asp Val Thr Cys Asn Ile Lys Asn Gly Arg Cys Glu Gln Phe
130                 135                 140
Cys Lys Asn Ser Ala Asp Asn Lys Val Val Cys Ser Cys Thr Glu Gly
145                 150                 155                 160
Tyr Arg Leu Ala Glu Asn Gln Lys Ser Cys Glu Pro Ala Val Pro Phe
                165                 170                 175
Pro Cys Gly Arg Val Ser Val Ser Gln Thr Ser Lys Leu Thr Arg Ala
                180                 185                 190
Glu Ala Val Phe Pro Asp Val Asp Tyr Val Asn Pro Thr Glu Ala Glu
                195                 200                 205
Thr Ile Leu Asp Asn Ile Thr Gln Gly Thr Gln Ser Phe Asn Asp Phe
210                 215                 220
Thr Arg Val Val Gly Gly Glu Asp Ala Lys Pro Gly Gln Phe Pro Trp
225                 230                 235                 240
Gln Val Val Leu Asn Gly Lys Val Asp Ala Phe Cys Gly Gly Ser Ile
                245                 250                 255
Val Asn Glu Lys Trp Ile Val Thr Ala Ala His Cys Val Glu Thr Gly
                260                 265                 270
Val Lys Ile Thr Val Val Ala Gly Glu His Asn Ile Glu Glu Thr Glu
                275                 280                 285
His Thr Glu Gln Lys Arg Asn Val Ile Arg Ile Pro His His Asn
290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
                340                 345                 350
Val Ser Gly Trp Ala Arg Val Phe His Lys Gly Arg Ser Ala Leu Val
                355                 360                 365
Leu Gln Tyr Leu Arg Val Pro Leu Val Asp Arg Ala Thr Cys Leu Arg
370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
                420                 425                 430
Glu Glu Cys Ala Met Lys Gly Lys Tyr Gly Ile Tyr Thr Lys Val Ser

```
                      435                 440                 445
Arg Tyr Val Asn Trp Ile Lys Glu Lys Thr Lys Leu Thr
    450                 455                 460

<210> SEQ ID NO 20
<211> LENGTH: 676
<212> TYPE: PRT
<213> ORGANISM: Homo sapiens

<400> SEQUENCE: 20

Met Arg Val Leu Gly Gly Arg Cys Gly Ala Pro Leu Ala Cys Leu Leu
1               5                   10                  15

Leu Val Leu Pro Val Ser Glu Ala Asn Phe Leu Ser Lys Gln Gln Ala
            20                  25                  30

Ser Gln Val Leu Val Arg Lys Arg Ala Asn Ser Leu Leu Glu Glu
        35                  40                  45

Thr Lys Gln Gly Asn Leu Glu Arg Glu Cys Ile Glu Glu Leu Cys Asn
50                  55                  60

Lys Glu Glu Ala Arg Glu Val Phe Glu Asn Asp Pro Glu Thr Asp Tyr
65                  70                  75                  80

Phe Tyr Pro Lys Tyr Leu Val Cys Leu Arg Ser Phe Gln Thr Gly Leu
                85                  90                  95

Phe Thr Ala Ala Arg Gln Ser Thr Asn Ala Tyr Pro Asp Leu Arg Ser
            100                 105                 110

Cys Val Asn Ala Ile Pro Asp Gln Cys Ser Pro Leu Pro Cys Asn Glu
        115                 120                 125

Asp Gly Tyr Met Ser Cys Lys Asp Gly Lys Ala Ser Phe Thr Cys Thr
130                 135                 140

Cys Lys Pro Gly Trp Gln Gly Glu Lys Cys Glu Phe Asp Ile Asn Glu
145                 150                 155                 160

Cys Lys Asp Pro Ser Asn Ile Asn Gly Gly Cys Ser Gln Ile Cys Asp
                165                 170                 175

Asn Thr Pro Gly Ser Tyr His Cys Ser Cys Lys Asn Gly Phe Val Met
            180                 185                 190

Leu Ser Asn Lys Lys Asp Cys Lys Asp Val Asp Glu Cys Ser Leu Lys
        195                 200                 205

Pro Ser Ile Cys Gly Thr Ala Val Cys Lys Asn Ile Pro Gly Asp Phe
210                 215                 220

Glu Cys Glu Cys Pro Glu Gly Tyr Arg Tyr Asn Leu Lys Ser Lys Ser
225                 230                 235                 240

Cys Glu Asp Ile Asp Glu Cys Ser Glu Asn Met Cys Ala Gln Leu Cys
                245                 250                 255

Val Asn Tyr Pro Gly Gly Tyr Thr Cys Tyr Cys Asp Gly Lys Lys Gly
            260                 265                 270

Phe Lys Leu Ala Gln Asp Gln Lys Ser Cys Glu Val Val Ser Val Cys
        275                 280                 285

Leu Pro Leu Asn Leu Asp Thr Lys Tyr Glu Leu Leu Tyr Leu Ala Glu
290                 295                 300

Gln Phe Ala Gly Val Val Leu Tyr Leu Lys Phe Arg Leu Pro Glu Ile
305                 310                 315                 320

Ser Arg Phe Ser Ala Glu Phe Asp Phe Arg Thr Tyr Asp Ser Glu Gly
                325                 330                 335

Val Ile Leu Tyr Ala Glu Ser Ile Asp His Ser Ala Trp Leu Leu Ile
            340                 345                 350

Ala Leu Arg Gly Gly Lys Ile Glu Val Gln Leu Lys Asn Glu His Thr
```

```
                355                 360                 365
Ser Lys Ile Thr Thr Gly Gly Asp Val Ile Asn Asn Gly Leu Trp Asn
        370                 375                 380

Met Val Ser Val Glu Glu Leu Glu His Ser Ile Ser Ile Lys Ile Ala
385                 390                 395                 400

Lys Glu Ala Val Met Asp Ile Asn Lys Pro Gly Pro Leu Phe Lys Pro
                405                 410                 415

Glu Asn Gly Leu Leu Glu Thr Lys Val Tyr Phe Ala Gly Phe Pro Arg
            420                 425                 430

Lys Val Glu Ser Glu Leu Ile Lys Pro Ile Asn Pro Arg Leu Asp Gly
        435                 440                 445

Cys Ile Arg Ser Trp Asn Leu Met Lys Gln Gly Ala Ser Gly Ile Lys
    450                 455                 460

Glu Ile Ile Gln Glu Lys Gln Asn Lys His Cys Leu Val Thr Val Glu
465                 470                 475                 480

Lys Gly Ser Tyr Tyr Pro Gly Ser Gly Ile Ala Gln Phe His Ile Asp
                485                 490                 495

Tyr Asn Asn Val Ser Ser Ala Glu Gly Trp His Val Asn Val Thr Leu
            500                 505                 510

Asn Ile Arg Pro Ser Thr Gly Thr Gly Val Met Leu Ala Leu Val Ser
        515                 520                 525

Gly Asn Asn Thr Val Pro Phe Ala Val Ser Leu Val Asp Ser Thr Ser
    530                 535                 540

Glu Lys Ser Gln Asp Ile Leu Leu Ser Val Glu Asn Thr Val Ile Tyr
545                 550                 555                 560

Arg Ile Gln Ala Leu Ser Leu Cys Ser Asp Gln Gln Ser His Leu Glu
                565                 570                 575

Phe Arg Val Asn Arg Asn Leu Glu Leu Ser Thr Pro Leu Lys Ile
            580                 585                 590

Glu Thr Ile Ser His Glu Asp Leu Gln Arg Gln Leu Ala Val Leu Asp
        595                 600                 605

Lys Ala Met Lys Ala Lys Val Ala Thr Tyr Leu Gly Gly Leu Pro Asp
    610                 615                 620

Val Pro Phe Ser Ala Thr Pro Val Asn Ala Phe Tyr Asn Gly Cys Met
625                 630                 635                 640

Glu Val Asn Ile Asn Gly Val Gln Leu Asp Leu Asp Glu Ala Ile Ser
                645                 650                 655

Lys His Asn Asp Ile Arg Ala His Ser Cys Pro Ser Val Trp Lys Lys
            660                 665                 670

Thr Lys Asn Ser
        675

<210> SEQ ID NO 21
<211> LENGTH: 6
<212> TYPE: PRT
<213> ORGANISM: Artificial
<220> FEATURE:
<223> OTHER INFORMATION: Secretion signal sequence

<400> SEQUENCE: 21

Arg Lys Arg Arg Lys Arg
1               5
```

CHIMERIC FACTOR VII MOLECULES

STATEMENT OF PRIORITY

This application claims the benefit, under 35 U.S.C. §119 (e), of U.S. Provisional Application Ser. No. 61/220,278, filed Jun. 25, 2009, the entire contents of which are incorporated by reference herein.

STATEMENT OF GOVERNMENT SUPPORT

This invention was made with government support under grant number 5-P01-HL06350 awarded by the National Institutes of Health. The United States Government has certain rights in the invention.

FIELD OF THE INVENTION

The present invention relates to chimeric human coagulation Factor VII (FVII) polypeptides having greater coagulant activity and fewer thrombotic complications than presently available Factor VII polypeptides, as well as polynucleotide constructs encoding such polypeptides, vectors and host cells comprising and expressing the polynucleotides, pharmaceutical compositions, uses and methods of treatment.

BACKGROUND OF THE INVENTION

Blood coagulation is a process consisting of a complex interaction of various blood components (or factors) that eventually gives rise to a fibrin clot. Generally, the blood components, which participate in what has been referred to as the coagulation "cascade," are enzymatically inactive proteins (proenzymes or zymogens) that are converted to proteolytic enzymes by the action of an activator (which itself is an activated clotting factor). Coagulation factors that have undergone such a conversion are generally referred to as "active factors," and are designated by the addition of the letter "a" to the name of the coagulation factor (e.g., activated Factor VII is designated as Factor VIIa or FVIIa).

Normally, initiation of the haemostatic process is mediated by the formation of a complex between tissue factor and Factor VIIa. This complex then converts Factors IX (FIX) and X (FX) to their active forms. Factor Xa (FXa) converts limited amounts of prothrombin to thrombin on the tissue factor-bearing cell. Thrombin activates platelets and Factors V (FV) and VIII (FVIII) into Factors Va (FVa) and VIIIa (FVIIIa), both cofactors in the further process leading to the full thrombin burst. This process includes generation of Factor Xa by Factor IXa (FIXa) (in complex with Factor VIIIa) and occurs on the surface of activated platelets. Thrombin finally converts fibrinogen to fibrin resulting in formation of a fibrin clot. In recent years Factor VII and tissue factor have been found to be the main initiators of blood coagulation.

Factor VII is a plasma glycoprotein that circulates in blood as a single-chain zymogen. The zymogen has marginal catalytic activity. Single-chain Factor VII may be converted to two-chain Factor VIIa by Factor Xa, Factor XIIa, Factor IXa, Factor VIIa or thrombin in vitro. Factor Xa is believed to be the major physiological activator of Factor VII. Like several other plasma proteins involved in hemostasis, Factor VII is dependent on Vitamin K for its activity, which is required for the gamma-carboxylation of multiple glutamic acid residues that are clustered close to the amino terminus of the protein. These gamma-carboxylated glutamic acids are required for the metal ion-induced interaction of Factor VII with phospholipids. The conversion of zymogen Factor VII into the activated two-chain molecule occurs by cleavage of an internal $Arg_{152}$-$Ile_{153}$ peptide bond. Additionally, it is well known that high concentrations of Factor VII lead to autoactivation in vitro. In the presence of tissue factor, phospholipids and calcium ions, the two-chain Factor VIIa rapidly activates Factor X or Factor IX by limited proteolysis.

The gene coding for human FVII (hFVII) has been mapped to chromosome 13 at q34-qter 9 (de Grouchy et al., Hum Genet 1984; 66:230-233). It contains nine exons and spans 12.8 Kb (O'Hara et al., Proc Natl Acad Sci USA 1987; 84:5158-5162). The gene organization and protein structure of FVII are similar to those of other vitamin K-dependent procoagulant proteins, with exons 1a and 1b encoding for signal sequence; exon 2 the propeptide and GLA domain; exon 3 a short hydrophobic region; exons 4 and 5 the epidermal growth factor-like domains; and exon 6 through 8 the serine protease catalytic domain (Yoshitake et al., Biochemistry 1985; 24: 3736-3750).

Factor IX (Christmas factor) is the zymogen of a serine protease active in normal hemostasis and the enzymatic activity requires carboxylation of specific glutamic acid residues. Factors IX, X, VII and protein C are closely related paralogs of the same family of serine proteases, with a high degree of amino acid sequence identity and intron-exon arrangement of the genes coding for these proteins. These closely related proteins have a similar structure of functional domains from the amino to carboxyl terminus to include a γ-carboxyglutamic acid (GLA) domain, two epidermal growth factor-like (EGF) domains, an activation peptide and the catalytic domain. Protein S is a 666 amino acid, vitamin K-dependent protein with a GLA domain, 4 EGF-like domains, a thrombin sensitive region and 2 laminin domains.

The vitamin K dependent coagulation plasma proteins contain a GLA domain that functions as the site of protein attachment to membranes and the GLA domain is highly conserved among the various coagulation proteins. Despite their similarity, the GLA domains exhibit a wide range of affinities for phospholipid, with the GLA domain of Protein S having the highest affinity for phospholipids. (Ellison et al., Biochemistry, 1998; 37:7997-8003), (McDonald et al., Biochemistry 1997; 36:5120-27).

It is often desirable to stimulate or improve the coagulation cascade in a subject. Factor VIIa has been used to control bleeding disorders that have several causes such as clotting factor deficiencies (e.g., hemophilia A and B or deficiency of coagulation Factors XI or VII) or clotting factor inhibitors. Factor VIIa has also been used to control excessive bleeding occurring in subjects with a normally functioning blood clotting cascade (no clotting factor deficiencies or inhibitors against any of the coagulation factors). Such bleeding may, for example, be caused by a defective platelet function, thrombocytopenia or von Willebrand's disease.

Bleeding is also a major problem in connection with surgery and other forms of trauma. For example, Factor VII has been used extensively for treating soldiers wounded in Iraq and Afghanistan. (Perkins J G, et al. The Journal of Trauma. 2007; 62: 1095-9; discussion 9-101). Its use has been credited with saving many lives, but as with most medical treatments, there are side effects, such as stroke or other thrombotic events after treatment. The overall impression of physicians using FVIIa, however, is that its use has saved many more lives than it has lost. Perhaps the best indication of this is that in previous wars approximately 30 percent of the wounded died of their injuries, while the number in the current Gulf war has been reduced to about 10 percent. (Gawande A, et al., N Engl J Med. 2004; 351: 2471-5).

Studies of transgenic hemophilia B mice expressing factor VIIa have demonstrated that continuous Factor VIIa expression at low levels (below 1.5 µg/ml) restores clotting activity in hemophilia B mice. Levels of factor VIIa in wild type or hemophilia B mice above 2 µg/ml, however, led to thromboses in the heart and lungs; both the heart and lungs are sites of high tissue factor expression. This suggests that the high levels of factor VIIa in the circulation induce thrombosis when they contact tissue factor exposed upon vessel injury in the heart and lungs. (Margaritas et al., *J. Clin. Invest.* 2004; 113:1025-31). Furthermore, studies have shown that vector mediated gene transfer of canine Factor VIIa in hemophilic dogs is both safe and effective in the short and medium term. (Margaritas et al., *Gene Therapy* 2009; 113:3682-3689).

Warnings relating to treatment with Factor VII are currently proposed for products seeking regulatory approval. For example, The European Medicines Agency, Human Medicines Evaluation Unit recommends that current Factor VII therapies carry a warning of the risk of thrombosis and disseminated intravascular coagulation, particularly in situations where the Factor VII is to be administered to patients with a history of coronary heart disease or liver disease, post-operative patients, neonates and those at risk from thrombosis and disseminated intravascular coagulation. See, e.g., *Core SPC for Human Plasma Derived Coagulation Factor VII Products* (CPMP/BPWG/2048/01), July, 2004.

Previously, it has been shown that the EGF-1 domain of Factor VIIa plays a critical role in the affinity of Factor VIIa for tissue factor. Using both a synthetic substrate and Factor X, in both the presence and absence of tissue factor, Factor VIIa polypeptides with a Factor IX EGF-1 domain had lower catalytic activity than the wild type Factor VIIa. (Jin et al., *Biochemistry,* 1999, 28:1185-92). At first glance, this would seem to obviate the use of chimeric constructs for treating bleeding; however, Monroe (*British Journal of Haematology* 1997; 99:542-549) has proposed that the mechanism of FVIIa in treating hemophilia and bleeding is tissue factor independent. Opinion in the art, however, is divided as to whether Factor VIIa is not active independent of tissue factor.

Commercial preparations of human recombinant FVIIa are sold as NovoSeven® and NovoSeven® RT. NovoSeven® and NovoSeven® RT are indicated for the treatment of bleeding episodes in hemophilia A or B patients and are the only rFVIIa for treatment of bleeding episodes available on the market. Recently, it has been demonstrated that NovoSeven® may bind to rehydrated lyophilized platelets, which could be administered in combination to localize the Factor VII to a site of injury. (Fischer et al., *Platelets,* 2008; 19:182-91). Additionally, it has been shown that selective PEGylation of Factor VII may increase plasma half-life, (Stennicke et al., *Thromb. Haemost,* 2008; 100:920-28), and that a recombinant human Factor VII, with 3 amino acid substitutions has an increased activity on the surface of platelets. (Moss et al., *J. Thromb. Haemost.,* 2009; 7:299-305). PEGylation of the chimeric Factor VIIa molecules of the present invention are expected to work in a similar manner to increase plasma half-life. Likewise, other modifications of proteins known in the art, such as covalent attachment of non-polypeptide moieties to form conjugates, e.g., glycosylation, are expected to function in a similar manner in the chimeric Factor VIIa molecules of the present invention, i.e., the properties imparted to a protein by the covalent attachment of a non-polypeptide moiety are expected to be imparted to the chimeric Factor VII a molecules.

There is a need for variants of Factor VIIa having high coagulant activity that can be administered at relatively low doses, and variants which produce fewer undesirable side effects such as thrombotic complications, associated with available therapies.

SUMMARY OF THE INVENTION

This application discloses chimeric FVIIa molecules, in particular chimeric hFVIIa molecules comprising hFVIIa domains and domains from one or more proteins of the coagulation system, providing one or more desired benefits. The chimeric FVIIa molecules of the present invention, therefore, have one or more improved properties as compared to commercially available rFVIIa, including having higher coagulant activity and/or being able to be administered at relatively low doses and/or producing fewer thrombotic complications. Consequently, medical treatment with a chimera of the invention offers advantages over the currently available rFVIIa compound, such as potentially lower doses and/or fewer undesirable side effects.

Representative chimeric FVIIa polypeptides of the invention include a chimeric FVIIa comprising the EGF-2 and catalytic domains of FVII and the GLA domain of a vitamin K-dependent coagulation protein and the EGF-1 domain of a vitamin K-dependent coagulation protein. In particular embodiments of the invention chimeric FVIIa polypeptides of the invention include 1) a chimeric FVIIa comprising the GLA and EGF-1 domains of FIX and the EGF-2 and catalytic domains of FVII; 2) a chimeric FVIIa comprising the EGF-1 domain of FIX and the GLA, EGF-2 and catalytic domains of FVII; 3) a chimeric FVIIA comprising the GLA domain of Protein S, the EGF-1 domain of FIX and the EGF-2 and catalytic domains of FVII; 4) a chimeric FVIIa comprising the GLA and EGF-1 domains of Protein S and the EGF-2 and catalytic domains of FVII; 5) a chimeric FVIIa comprising the EGF-1 domain of Protein S and the GLA, EGF-2 and catalytic domains of FVII; and 6) a chimeric FVIIa comprising the EGF-1 domain of Protein S, the GLA domain of FIX and the EGF-2 and catalytic domains of FVII. Representative chimeric FVIIa polypeptides of the invention also may include wild-type FVIIa or any of the above described chimeric FVIIa polypeptides, which have amino acid substitutions in the EGF-1 domain or the GLA domain. The substitutions can be conservative substitutions or non-conservative substitutions. Such substitutions may include the substitution of the isoleucine at residue 69 by alanine and/or a substitution of the arginine at residue 79 by alanine of the EGF-1 domain. Additional substitutions may include the substitution of the lysine at residue 5 by arginine, which causes the GLA domain to have a higher binding affinity for collagen type IV but does not appear to affect platelet binding (Gui et al., *J. Thromb Haemost.* 2009; 7:1843-1851); the substitution of the methionine at residue 306 by another amino acid, preferably a conservative amino acid substation, more preferably alanine, which further reduces the affinity for tissue factor; and, the substitution of the valine at residue 158 by aspartate, the substitution of the glutamate at 296 by valine and/or the substitution of the methionine at residue 298 by glutamine, which result in a Factor VIIa with higher specific activity.

Also provided are methods of treating a bleeding disorder in a subject having the bleeding disorder by administering one or more of the herein described chimeric FVIIa polypeptides. The method of treating the bleeding disorder may include a method of administering to the subject a nucleic acid molecule comprising a nucleotide sequence encoding a chimeric Factor VIIa polypeptide of this invention.

Additionally, the invention provides a method of treating a bleeding disorder in a subject having the bleeding disorder by administering a protein comprising a GLA domain, wherein the protein is targeted to and/or concentrated near the site of a clot in relation to the concentration of the protein in circulation in the subject's plasma. This may include using domains that bind with greater affinity to platelets, which are found at or near the site of clot formation, than the currently available Factor VII polypeptides. Examples of such domains are the GLA domains of various coagulation proteins that bind the negatively charged phospholipid layers located on the surface of platelets. Nonlimiting examples of such GLA domains include the GLA domain of FIX, which binds much tighter than the GLA domain of FVIIa to platelets and phospholipids (Melton et al. "Location of the platelet binding site in zymogen coagulation factor IX" *Blood Coagul Fibrinolysis* 12:237-243 (2001)) and the GLA domain of protein S, which binds phospholipids tighter than any other known GLA domain (McDonald et al. "Comparison of naturally occurring vitamin K-dependent proteins: correlation of amino acid sequences and membrane binding properties suggests a membrane contact site" *Biochemistry*:36:5120-5127 (1997)). Nonlimiting examples of a protein comprising a GLA domain include a recombinant protein comprising a GLA domain of FIX or Protein S, a chimeric protein comprising a GLA domain of FIX or Protein S and/or a chimeric FVIIa polypeptide of this invention comprising a GLA domain of FIX or Protein S.

In another embodiment, the present invention provides a method of treating a subject having a bleeding disorder by administering a chimeric Factor VIIa polypeptide of the invention that comprises a catalytic domain derived from a Factor VII polypeptide and a platelet targeting domain, or domains. Such platelet targeting domains include domains from proteins that interact or bind to the surface of a platelet. Such interaction or binding to the surface of a platelet can be mediated through the membrane phospholipids of the platelet, or through platelet cell surface proteins and/or receptors. Nonlimiting examples of such domains include the A1 domain of von Willebrand Factor, which is the principal binding site for platelet glycoprotein Ib (Emsley et al., *JBC*, 273: 10396-10401 (1998)) and the Fab fragment (domain) of antibodies that binds to platelet membrane proteins and/or receptors, such as an antibody that binds to platelet membrane phospholipids (Out et al., *Blood*, 77:2655-2659 (1991)).

Such targeting of coagulation proteins to the site of a clot using a domain that binds to platelets and has reduced affinity for tissue factor has the additional, but unexpected benefit of decreasing the risk of complications associated with current Factor VII therapies, such as thrombogenicity. This approach can also be used to target other therapeutically useful polypeptides or other molecules to platelets, or the site of a clot. Such therapeutically useful molecules may include anticoagulants and the like.

The present invention further provides a method of treating a bleeding disorder in a subject having the bleeding disorder by administering to the subject a polypeptide with reduced thrombogenicity in relation to the thrombogenicity of Factor VII (e.g., reduced at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 90%, etc. in relation to the thrombogenicity of native Factor VII). "Reduced thrombogenicity" can be determined in a variety of ways according to art-known methods, including but not limited to a determination of a reduced number of clots, smaller clots, longer time required for clots to occur (in vivo or in an in vitro assay, fewer subject deaths due to thrombus formation and/or extended survival time, as compared to control. A polypeptide with reduced thrombogenicity as compared with Factor VII can be, for example, a chimeric Factor VII polypeptide of this invention or active fragment thereof. Nonlimiting examples of such polypeptides include a chimeric FVIIa comprising the GLA and EGF-1 domains of FIX and the EGF-2 and catalytic domains of FVII and a chimeric FVIIa comprising the GLA domain of Protein S, the EGF-1 domain of FIX and the EGF-2 and catalytic domains of FVII.

BRIEF DESCRIPTION OF THE DRAWINGS

FIG. 6 shows the sequence of an exemplary chimeric Factor VII of the present invention, comprising the signal, pro peptide, GLA and EGF1 domains of Factor IX (underlined) (SEQ ID NO:1), FIG. 7 shows the sequence of an exemplary chimeric Factor VII of the present invention, comprising the signal, pro peptide, and EGF1 domains of Factor IX (underlined), and the GLA domain of Protein S (bold) (SEQ ID NO:2).

DESCRIPTION OF THE INVENTION

Figure 1:
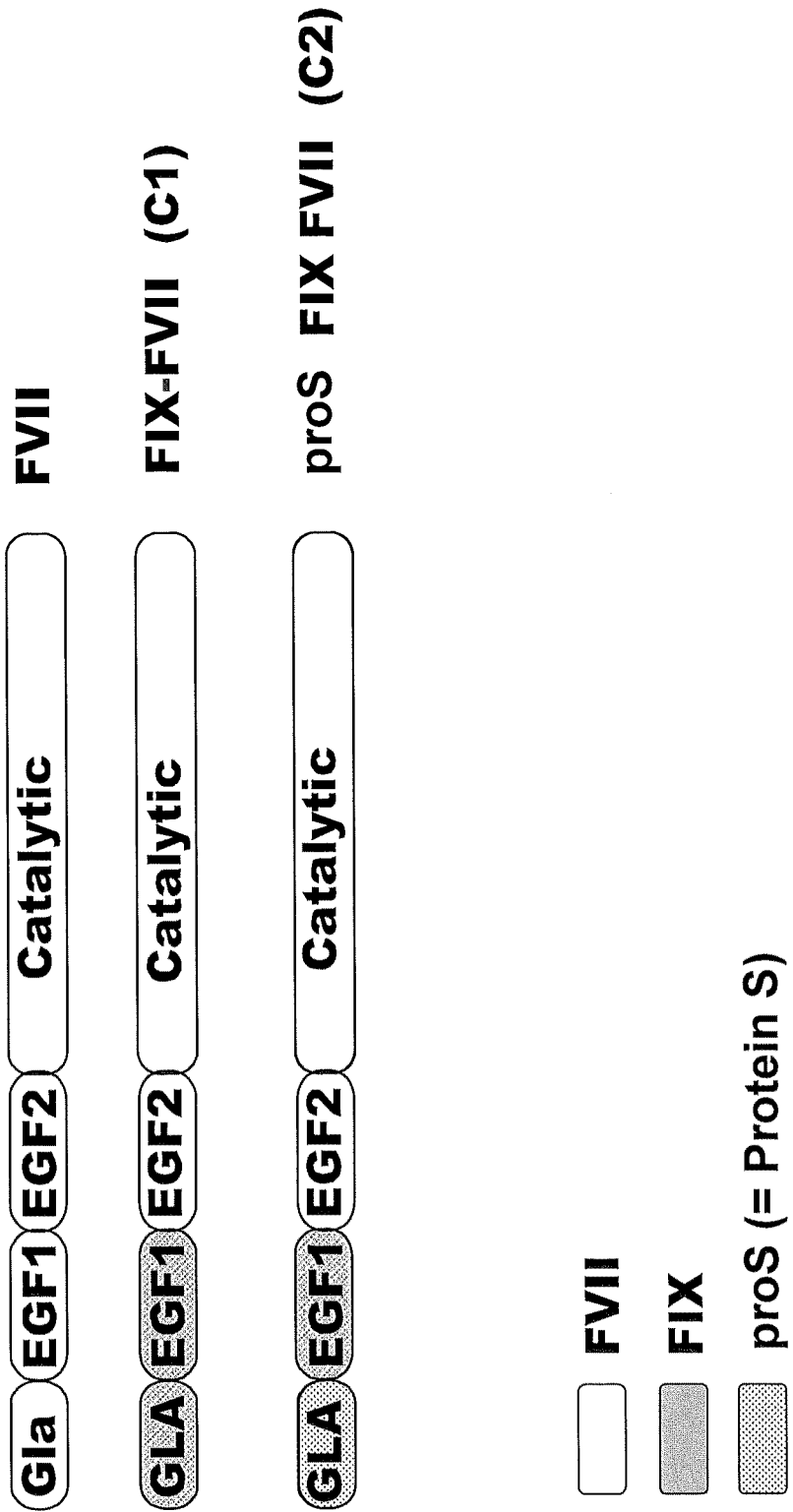
FIG. 1 shows a diagrammatic representation of chimeric FVIIa molecules useful in the present invention. FVII: Factor VII; FIX: Factor IX

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference herein in their entirety.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "about," as used herein when referring to a measurable value such as an amount or concentration and the like, is meant to encompass variations of 20%, 10%, 5%, 1%, 0.5%, or even 0.1% of the specified amount.

The term "activity" as used herein means the ability of a Factor VII polypeptide to convert its substrate Factor X to the active Factor Xa.

The term "inherent activity" also includes the ability to generate thrombin on the surface of activated platelets in the absence of tissue factor.

The term "N-terminal GLA-domain" includes the amino acid sequence from about amino acid residue 61 to about amino acid residue 105 of the amino acid sequence SEQ ID NO:18), the amino acid sequence from about amino acid residue 47 to about amino acid residue 92 of the amino acid sequence of SEQ ID NO:19, any post-translational modifications to the identified amino acid sequences, any conservative amino acid substitutions in the identified amino acid sequences, addition of amino acid residues to the identified amino acid sequences, deletions of amino acid residues from the identified amino acid sequences, or any other amino acid sequence from a coagulation cascade protein that binds to phospholipid membranes.

The term "EGF-1" describes a region of 30-40 amino acids containing six cysteines found originally in EGF (epidermal growth factor) and also in a range of proteins involved in cell signaling and in coagulation proteins, with nearly all known EGF-like domains containing disulfide bonds 1-3, 2-4 and 5-6. The EGF-1 domain of Factor VII is from about amino acid residue 106 to about amino acid residue 142 of the amino acid sequence of SEQ ID NO:18. The EGF-1 domain of Factor IX is from about amino acid residue 93 to about amino acid residue 129 of the amino acid sequence of SEQ ID NO:19. The EGF-1 domain of Protein S is from about amino acid residue 117 to about amino acid residue 155 of the amino acid sequence of SEQ ID NO:20. These amino acid sequences can include any post-translational modifications to the identified amino acid sequences, any conservative amino acid substitutions in the identified amino acid sequences, any addition of amino acid residues to the identified amino acid sequences and/or any deletions of amino acid residues from the identified amino acid sequences.

The term "EGF-2" means the second EGF-like domain in a series (of two or more EGF-like domains). The EGF-2 domain of Factor VII is from about amino acid residue 147 to about amino acid residue 188 in the amino acid sequence of SEQ ID NO:18. The EGF-2 domain of Factor IX is from about amino acid residue 130 to about amino acid residue 171 in the amino acid sequence of SEQ ID NO:19. The EGF-2 domain of Protein S is from about amino acid residue 157 to about amino acid residue 200 in the amino acid sequence of SEQ ID NO:20. These amino acid sequences can include any post-translational modifications to the identified amino acid sequences, any conservative amino acid substitutions in the identified amino acid sequences, any addition of amino acid residues to the identified amino acid sequences and/or any deletions of amino acid residues from the identified amino acid sequences.

The term "catalytic domain" as used herein means a domain in a protein that mediates cleavage of peptide bonds. The catalytic domain of Factor VII is from about amino acid residue 213 to about amino acid residue 452 in the amino acid sequence of SEQ ID NO:18. The catalytic domain of Factor IX is from about amino acid residue 227 to about amino acid residue 459 in the amino acid sequence of SEQ ID NO:19. These amino acid sequences can include any post-translational modifications to the identified amino acid sequences, any conservative amino acid substitutions in the identified amino acid sequences, any addition of amino acid residues to the identified amino acid sequences and/or any deletions of amino acid residues from the identified amino acid sequences.

The three-letter indication "GLA" means 4-carboxy-glutamic acid (γ-carboxyglutamate).

The term "protease domain" means a domain in a protein that mediates cleavage of peptide bonds, generally considered to be from about amino acid residue 213 to the carboxy terminal amino acid residue of SEQ ID NO:18. (the heavy-chain of Factor VIIa). The term "Factor VII polypeptide" as used herein means any protein comprising the amino acid sequence 61-466 of native human Factor VII (SEQ ID NO:18) or variants or fragments thereof. This includes but is not limited to human Factor VII, human Factor VIIa and variants thereof. The term "Factor VII" as used herein is intended to comprise the inactive one-chain zymogen Factor VII molecule as well as the activated two-chain Factor VII molecule (Factor VIIa). This includes proteins that have the amino acid sequence 61-466 (SEQ ID NO:18) of native human Factor VII or Factor VIIa. One of skill in the art recognizes that minor sequence changes would be expected to perform in a similar manner and that the domains, polypeptides and Factor VII involved could be slightly shortened or lengthened or contain substitutions without departing from the invention. Thus, the definition also encompasses proteins and peptides with a slightly modified amino acid sequence, for instance, a modified N-terminal end including N-terminal amino acid deletions or additions such that in some embodiments those proteins substantially retain the activity of Factor VIIa (e.g., retain about 50%, 60%, 70%, 80%, 90%, 95%, etc. of the activity of native Factor VIIa). The term "Factor VIIa," or "FVIIa" as used herein means a product consisting of the activated form (Factor VIIa). "Factor VII" or "Factor VIIa" within the above definition also includes natural allelic variations that may exist and occur from one individual to another. Also, degree and location of glycosylation or other post-translation modifications may vary depending on the chosen host cells, tissue, or animal species of expression and the nature of the host cellular, or tissue environment.

The term "domain" as used herein is intended to encompass a part of a protein sequence and structure that can evolve, function, and exist independently of the rest of the protein chain. A domain is capable of forming a compact three-dimensional structure and often can be independently stable and folded. One domain may appear in a variety of evolutionarily related proteins. Domains vary in length from between about 25 amino acids up to about 500 amino acids in length. A "domain" can also encompass a domain from a wild-type protein that has had an amino acid residue, or residues, replaced by conservative substitution. Because they are self-stable in a protein milieu, domains can be "swapped" by genetic engineering between one protein and another to make chimeric proteins.

The term "variant" or "variants," as used herein, is intended to designate Factor VII having the amino acid sequence 61-466 (SEQ ID NO:18) of native human Factor VII or Factor VIIa, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein and/or wherein the GLA domain has been substituted with a GLA domain from a different protein (e.g., a GLA domain that binds to platelet membranes or phospholipid membranes) and/or wherein the GLA domain has been substituted with a platelet-binding domain from a different protein (e.g., the A1 domain of von Willebrand Factor, which is the principal binding site for platelet glycoprotein Ib (Emsley et al., *JBC,* 273:10396-10401 (1998)) and the Fab fragment (domain) of antibodies that binds to platelet membrane proteins and/or receptors, such as an antibody that binds to platelet membrane phospholipids (Out et al., *Blood,* 77:2655-2659 (1991)) and/or wherein the EGF-1 domain of Factor VII has been substituted with an EGF-1 domain from a different protein (e.g., an EGF-1 domain that binds with lower affinity to tissue factor, such as the EGF-1 domain of Factor IX). Such addition can take place either at the N-terminal end or at the C-terminal end of the parent protein or both, as well as internally. Thus, in some embodiments, the "variant" or "variants" of this invention can still have FVII clotting activity in their activated form. In some embodiments, the variant or variants of this invention may not have clotting activity.

Thus, in some embodiments, a variant is at least, 40%, 50%, 60% or 70% identical with the amino acid sequence 61-466 (SEQ ID NO:18) of native human Factor VII or Factor VIIa. For example, the EGF-1 domain of FVII has 65.7% identity with the EGF-1 domain of FIX and the GLA domain of FVII has 58.6% identity with the GLA domain of FIX and 51% identity with the GLA domain of Protein S. In one embodiment a variant is at least 80% identical with the amino acid sequence 61-466 (SEQ ID NO:18) of native human Factor VII or Factor VIIa. In another embodiment a variant is at least 90% identical with the amino acid sequence 61-466 (SEQ ID NO:18) of native human Factor VII or Factor VIIa. In a further embodiment a variant is at least 95% identical with the amino acid sequence 61-466 (SEQ ID NO:18) of native human Factor VII or Factor VIIa.

The term "any other amino acid" as used herein means one amino acid that is different from that amino acid naturally present at that position. This includes but is not limited to amino acids that can be encoded by a polynucleotide. Preferably the different amino acid is in natural L-form and can be encoded by a polynucleotide. A specific example is L-cysteine (Cys).

As used herein, the term "operably linked" refers to the covalent joining of two or more nucleotide sequences, by means of enzymatic ligation or otherwise, in a configuration relative to one another such that the normal function of the sequences can be performed. For example, the nucleotide sequence encoding a presequence or secretory leader is operably linked to a nucleotide sequence coding for a polypeptide if it is expressed as a preprotein that participates in the secretion of the polypeptide: a promoter or enhancer is operably linked to a coding sequence if it affects the transcription of the sequence of interest; a ribosome binding site is operably linked to a coding sequence if it is positioned so as to facilitate translation into the protein or peptide of interest. Generally, "operably linked" means that the nucleotide sequences being linked are contiguous and in the case of a secretory leader, contiguous and in reading phase Linking is most easily accomplished by ligation at convenient restriction sites. If such sites do not exist, then synthetic oligonucleotide adaptors or linkers are used, in conjunction with standard recombinant DNA methods.

The term "vector," as used herein, means any nucleic acid entity capable of amplification in a host cell. Thus, the vector may be an autonomously replicating vector, i.e., a vector, which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to plasmid vectors, phage vectors, viruses or cosmid vectors. Vectors usually contain a replication origin and at least one selectable gene, i.e., a gene which encodes a product which is readily detectable or the presence of which is essential for cell growth.

The term "host cell," as used herein, represents any cell, including hybrid cells, in which heterologous DNA can be expressed. Typical host cells include, but are not limited to insect cells, yeast cells, mammalian cells, including human cells, such as BHK, CHO, HEK, and COS cells. In practicing the present invention, the host cells being cultivated are preferably mammalian cells, more preferably an established mammalian cell line, including, without limitation, CHO (e.g., ATCC CCL 61), COS-1 (e.g., ATCC CRL 1650), baby hamster kidney (BHK) and HEK293 (e.g., ATCC CRL 1573; Graham et al., *J. Gen. Virol.* 36:59-72, 1977) cell lines. A suitable BHK cell line is the tk$^{-ts13}$ BHK cell line (Waechter and Baserga, *Proc. Natl. Acad. Sci.* USA 79:1106-1110, 1982), hereinafter referred to as BHK 570 cells. The BHK 570 cell line is available from the American Type Culture Collection, 10801 University, Boulevard, Manassas, Va. 20110, under ATCC accession number CRL 10314. A tk-ts13 BHK cell line is also available from the ATCC under accession number CRL 1632. Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (Urlaub and Chasin, *Proc. Natl. Acad. Sci.* USA 77:4216-4220, 1980). Also useful are 3T3 cells, Namalwa cells, myelomas and fusions of myelomas with other cells.

As used herein the term "appropriate growth medium" means a medium containing nutrients and other components required for the growth of cells and the expression of the nucleic acid sequence encoding the Factor VII polypeptide of the invention.

The term "conjugate" (or interchangeably "conjugated polypeptide") is intended to indicate a heterogeneous (in the sense of composite or chimeric) molecule formed by the covalent attachment of one or more polypeptide(s) to one or more non-polypeptide moieties such as polymer molecules, lipophilic compounds, sugar moieties or organic derivatizing agents. Preferably, the conjugate is soluble at relevant concentrations and conditions, i.e., soluble in physiological fluids such as blood. Examples of conjugated polypeptides of the invention include glycosylated and/or PEGylated polypeptides.

The term "covalent attachment" means that the polypeptide and the non-polypeptide moiety are either directly covalently joined to one another, or else are indirectly covalently joined to one another through an intervening moiety or moieties, such as a bridge, spacer, or linkage moiety or moieties. The term "non-conjugated polypeptide" can be used to refer to the polypeptide part of the conjugate.

When used herein, the term "non-polypeptide moiety" means a molecule that is capable of conjugating to an attachment group of the polypeptide of the invention. Suitable examples of such molecules include polymer molecules, sugar moieties, lipophilic compounds, or organic derivatizing agents. When used in the context of a conjugate of the invention it will be understood that the non-polypeptide moiety is linked to the polypeptide part of the conjugate through an attachment group of the polypeptide. As explained above, the non-polypeptide moiety can be directly covalently joined to the attachment group or it can be indirectly covalently joined to the attachment group through an intervening moiety or moieties, such as a bridge, spacer, or linkage moiety or moieties.

The "polymer molecule" is a molecule formed by covalent linkage of two or more monomers, wherein none of the monomers is an amino acid residue, except where the polymer is human albumin or another abundant plasma protein. The term "polymer" can be used interchangeably with the term "polymer molecule." The term is intended to encompass carbohydrate molecules attached by in vitro glycosylation, i.e., a synthetic glycosylation performed in vitro normally involving covalently linking a carbohydrate molecule to an attachment group of the polypeptide, optionally using a cross-linking agent.

A carbohydrate molecule attached by in vivo glycosylation, such as N- or O-glycosylation (as further described below) is referred to herein as a "sugar moiety." Except where the number of non-polypeptide moieties, such as polymer molecule(s) or sugar moieties in the conjugate is expressly indicated every reference to "a non-polypeptide moiety" contained in a conjugate or otherwise used in the present invention shall be a reference to one or more non-polypeptide moieties, such as polymer molecule(s) or sugar moieties.

The term "attachment group" is intended to indicate a functional group of the polypeptide, in particular of an amino acid residue thereof or a carbohydrate moiety, capable of attaching a non-polypeptide moiety such as a polymer molecule, a lipophilic molecule, a sugar moiety or an organic derivatizing agent.

For in vivo N-glycosylation, the term "attachment group" is used in an unconventional way to indicate the amino acid residues constituting a N-glycosylation site (with the sequence N-X-S/T/C, wherein X is any amino acid residue except proline, N is asparagine and S/T/C is either serine, threonine or cysteine, preferably serine or threonine, and most preferably threonine). Although the asparagine residue of the N-glycosylation site is the one to which the sugar moiety is attached during glycosylation, such attachment cannot be achieved unless the other amino acid residues of the N-glycosylation site are present.

Accordingly, when the non-polypeptide moiety is a sugar moiety and the conjugation is to be achieved by N-glycosylation, the term "amino acid residue comprising an attachment group for the non-polypeptide moiety" as used in connection with alterations of the amino acid sequence of the polypeptide of interest is to be understood as meaning that one or more amino acid residues constituting an N-glycosylation site are to be altered in such a manner that either a functional N-glycosylation site is introduced into the amino acid sequence or removed from said sequence.

In the present context, the term "treat" or "treatment" is meant to include both control and/or prevention of an expected bleeding, such as in surgery, and regulation of an already occurring bleeding, such as in trauma or in on demand treatment for hemophilia patients, with the purpose of inhibiting or minimizing the bleeding. Prophylactic administration of the Factor VIIa polypeptide according to the invention is thus included in the term "treatment."

The term "bleeding episode" is meant to include uncontrolled and excessive bleeding. Bleeding episodes may be a major problem both in connection with surgery and other forms of tissue damage. Uncontrolled and excessive bleeding may occur in subjects having a normal coagulation system and subjects having coagulation or bleeding disorders.

As used herein the term "bleeding disorder" reflects any defect, congenital, acquired or induced, of cellular, physiological, or molecular origin that is manifested in bleedings. Examples are clotting factor deficiencies (e.g., hemophilia A and B or deficiency of coagulation Factors XI or VII), clotting factor inhibitors, defective platelet function, thrombocytopenia, von Willebrand's disease, or bleeding induced by surgery or trauma.

Excessive bleedings also occur in subjects with a normally functioning blood clotting cascade (no clotting factor deficiencies or inhibitors against any of the coagulation factors) and may be caused by a defective platelet function, thrombocytopenia or von Willebrand's disease. In such cases, the bleedings may be likened to those bleedings caused by hemophilia because the haemostatic system, as in hemophilia, lacks or has abnormal essential clotting "compounds" (such as platelets or von Willebrand factor protein), causing major bleedings. In subjects who experience extensive tissue damage in association with surgery or trauma, the normal haemostatic mechanism may be overwhelmed by the demand of immediate hemostasis and they may develop bleeding in spite of a normal haemostatic mechanism. Achieving satisfactory hemostasis also is a problem when bleedings occur in organs such as the brain, inner ear region and eyes, with limited possibility for surgical hemostasis. The same problem may arise in the process of taking biopsies from various organs (liver, lung, tumor tissue, gastrointestinal tract) as well as in laparoscopic surgery. Common for all these situations is the difficulty to provide hemostasis by surgical techniques (sutures, clips, etc.), which also is the case when bleeding is diffuse (hemorrhagic gastritis and profuse uterine bleeding). Acute and profuse bleedings may also occur in subjects on anticoagulant therapy in whom a defective hemostasis has been induced by the therapy given. Such subjects may need surgical interventions in case the anticoagulant effect has to be counteracted rapidly. Radical retropubic prostatectomy is a commonly performed procedure for subjects with localized prostate cancer. The operation is frequently complicated by significant and sometimes massive blood loss. The considerable blood loss during prostatectomy is mainly related to the complicated anatomical situation, with various densely vascularized sites that are not easily accessible for surgical hemostasis, and which may result in diffuse bleeding from a large area. Also, intracerebral hemorrhage is the least treatable form of stroke and is associated with high mortality and hematoma growth in the first few hours following intracerebral hemorrhage. Treatment with rFVIIa can limit the growth of the hematoma, reduce mortality, and improve functional outcomes at 90 days. With currently available rFVIIa, however, there is a risk of thromboembolic adverse events. The chimeric Factor VII molecules of the present invention, with lower thrombogenicity, can overcome this problem in stroke therapy. Another situation that may cause problems in the case of unsatisfactory hemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

In one embodiment of the invention, the bleeding is associated with hemophilia. In another embodiment, the bleeding is associated with hemophilia with acquired inhibitors. In another embodiment, the bleeding is associated with thrombocytopenia. In another embodiment, the bleeding is associated with von Willebrand's disease. In another embodiment, the bleeding is associated with severe tissue damage. In another embodiment, the bleeding is associated with severe trauma. In another embodiment, the bleeding is associated with surgery. In another embodiment, the bleeding is associated with laparoscopic surgery. In another embodiment, the bleeding is associated with hemorrhagic gastritis. In another embodiment, the bleeding is profuse uterine bleeding. In another embodiment, the bleeding is occurring in organs with a limited possibility for mechanical hemostasis. In another embodiment, the bleeding is occurring in the brain, inner ear region or eyes. In another embodiment, the bleeding is associated with the process of taking biopsies. In another embodiment, the bleeding is associated with anticoagulant therapy.

The term "subject" as used herein is intended to mean any animal, in particular mammals, such as humans, and may, where appropriate, be used interchangeably with the term "patient."

The term "enhancement of the normal haemostatic system" means an improvement of the ability to generate thrombin or to generate a functional clot.

The term "gene therapy" refers to a method of changing the expression of an endogenous gene by exogenous administration of a gene. As used herein, "gene therapy" also refers to the replacement of defective gene encoding a defective protein, or replacement of a missing gene, by introducing a functional gene corresponding to the defective or missing gene into somatic or stem cells of an individual in need. Gene therapy can be accomplished by ex vivo methods, in which differentiated or somatic stem cells are removed from the individual's body followed by the introduction of a normal copy of the defective gene into the explanted cells using a viral vector as the gene delivery vehicle. In addition, in vivo direct gene transfer technologies allow for gene transfer into cells in the individual in situ using a broad range of viral vectors, liposomes, protein DNA complexes or naked DNA in order to achieve a therapeutic outcome. The term "gene therapy" also refers to the replacement of a defective gene encoding a defective protein by introducing a polynucleotide that functions substantially the same as the defective gene or protein should function if it were not defective into somatic or stem cells of an individual in need.

In the present invention, gene therapy is employed in the context of administering to a subject a nucleic acid molecule comprising a nucleotide sequence encoding a chimeric FVII of this invention. Thus, the present invention provides an isolated nucleic acid molecule comprising a nucleotide sequence encoding a chimeric FVII protein of this invention. Such a nucleic acid molecule can be present in a nucleic acid construct (e.g., a vector or plasmid). Such a nucleic acid construct can be present in a cell. Further provided herein is a method of delivering a chimeric FVII protein of this invention to a cell, comprising introducing into the cell a nucleic acid molecule comprising a nucleotide sequence encoding the chimeric FVII protein under conditions whereby the nucleotide sequence is expressed to produce the chimeric FVII protein in the cell. The cell can be a cell that is introduced into a subject and/or the cell can be a cell already present in the subject.

Preparation of Chimeric Factor VII

The chimeric Factor VII polypeptides described herein may be produced by means of recombinant nucleic acid techniques. In general, a cloned wild-type Factor VII nucleic acid sequence is modified to encode the desired protein. This modified sequence is then inserted into an expression vector, which is in turn transformed or transfected into host cells. Higher eukaryotic cells, in particular cultured mammalian cells, are suitable as host cells. The complete nucleotide and amino acid sequences for human Factor VII are known (see U.S. Pat. No. 4,784,950, where the cloning and expression of recombinant human Factor VII is described, and GenBank® Accession Nos. J02933 and AAA51983 and SwissProt Accession No. P08709-1) and the amino acid sequence is provided herein as SEQ ID NO:18. The bovine Factor VII sequence is described in Takeya et al., *J. Biol. Chem.* 263: 14868-14872 (1988)). The complete nucleotide and amino acid sequences for Factor IX are known (see Davie et al., *Proc. Natl. Acad. Sci. U.S.A* 1982; 79:6461-6464; Jaye et al., *Nucleic Acids Res.* 1983; 11:2325-2335; and, McGraw et al., *Proc. Natl. Acad. Sci. U.S.A.* 1985; 82:2847-2851 and GenBank® Accession Nos. J00136 and AAA98726 and SwissProt Accession No. P00740) and the amino acid sequence is provided herein as SEQ ID NO:19; as are the complete nucleotide and amino acid sequences for Protein S (see Hoskins et al., *Proc. Natl. Acad. Sci. U.S.A.* 1987; 84:349-353 and GenBank® Accession Nos. M15036 and AAA36479 and SwissProt Accession No. P07225) and the amino acid sequence is provided herein as SEQ ID NO:20. The complete nucleotide and amino acid sequences for other coagulation proteins are also known and can be viewed using SwissProt or at the NCBI web page.

The amino acid sequence alterations may be accomplished by a variety of techniques. Modification of the nucleic acid sequence may be by site-specific mutagenesis. Techniques for site-specific mutagenesis are well known in the art and are described in, for example, Zoller and Smith (*DNA* 3:479-488, 1984) or "Splicing by extension overlap", Horton et al., *Gene* 77, 1989, pp. 61-68. Thus, using the nucleotide and amino acid sequences of Factor VII, one may introduce the alteration(s) of choice. Likewise, procedures for preparing a DNA construct using polymerase chain reaction using specific primers are well known to persons skilled in the art (see, *PCR Protocols,* 1990, Academic Press, San Diego, Calif., USA). Additionally, the chimeric Factor VII polypeptides of the present invention may be prepared by introducing unique restriction sites into the nucleotide sequences encoding the various polypeptides, which can be used to isolate fragments of nucleotide sequences that encode entire domains of various polypeptides. Subsequently, these various nucleotide sequences can be recombined to produce the various chimeric Factor VII polypeptides of the present invention.

For example, unique restriction sites may be introduced into the nucleotide sequences encoding various coagulation proteins so that the GLA, EGF-1, EGF-2 and catalytic domains may be freely interchanged between the various coagulation proteins. The EGF-1 domain can rotate freely around the EGF-2 domain, (Pike et al. *Proc Natl. Acad. Sci.* 1999; 96:8925-8930) whereas, the GLA and EGF-1 domains may not rotate freely around each other when calcium is present (Sunnerhagen et al. *Nature Structural Biology* 1995; 2:504-509). In this embodiment, the GLA and EGF-1 domains may be from the same coagulation protein, but from a different protein than the EGF-2 and catalytic domains. The chimeric Factor VIIa polypeptides of the present invention, may therefore, comprise domains from any of the coagulation proteins, provided at least 50% of one domain is a Factor VII domain. Further, the chimeric Factor VIIa polypeptides of the present invention may include GLA and EGF-1 domains from the same protein, or from different proteins.

The nucleic acid construct encoding the chimeric Factor VII polypeptides of the invention may suitably be of genomic or cDNA origin, for instance obtained by preparing a genomic or cDNA library and screening for DNA sequences coding for all or part of the various polypeptides by hybridization using synthetic oligonucleotide probes in accordance with standard techniques (see, Sambrook et al., *Molecular Cloning: A Laboratory Manual,* 2nd. Ed. Cold Spring Harbor Laboratory, Cold Spring Harbor, N.Y., 1989).

The nucleic acid construct encoding the chimeric Factor VII polypeptides may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. According to the phosphoamidite method, oligonucleotides are synthesized, e.g., in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

DNA sequences for use in producing chimeric Factor VII polypeptides according to the present invention will typically encode a pre-pro polypeptide at the amino-terminus of Factor VII to obtain proper posttranslational processing (e.g., gamma-carboxylation of glutamic acid residues) and secretion from the host cell. The pre-pro polypeptide may be that of Factor VII or another vitamin K-dependent plasma protein, such as Factor IX, Factor X, prothrombin, protein C or protein S. As will be appreciated by those skilled in the art, additional modifications can be made in the amino acid sequence of the chimeric Factor VII polypeptides where those modifications do not significantly impair the ability of the protein to act as a coagulant.

Expression vectors for use in expressing Factor VIIa variants will comprise a promoter capable of directing the transcription of a cloned gene or cDNA. Suitable promoters for use in cultured mammalian cells include viral promoters and cellular promoters. Viral promoters include the SV40 promoter (Subramani et al., *Mol. Cell. Biol.* 1:854-864, 1981) and the CMV promoter (Boshart et al., *Cell* 41:521-530, 1985). A particularly suitable viral promoter is the major late promoter from adenovirus 2 (Kaufman and Sharp, *Mol. Cell. Biol.* 2:1304-1319, 1982). Another particularly preferable promoter is the Chinese Hamster elongation factor-1-alpha (CHEF1) promoter. Cellular promoters include the mouse kappa gene promoter (Bergman et al., *Proc. Natl. Acad. Sci. USA* 81:7041-7045, 1983) and the mouse $V_H$ promoter (Loh et al., *Cell* 33:85-93, 1983). A particularly suitable cellular promoter is the mouse metallothionein-I promoter (Palmiter et al., *Science* 222:809-814, 1983). Expression vectors may also contain a set of RNA splice sites located downstream from the promoter and upstream from the insertion site for the chimeric Factor VII sequence itself. Suitable RNA splice sites may be obtained from adenovirus and/or immunoglobulin genes. Also contained in the expression vectors is a polyadenylation signal located downstream of the insertion site. Particularly suitable polyadenylation signals include the early or late polyadenylation signal from SV40 (Kaufman and Sharp), the polyadenylation signal from the adenovirus 5 Elb region, the human growth hormone gene terminator (DeNoto et al. *Nucl. Acids Res.* 9:3719-3730, 1981) or the polyadenylation signal from the human Factor VII gene or the bovine Factor VII gene. The expression vectors may also include a noncoding viral leader sequence, such as the adenovirus 2 tripartite leader, located between the promoter and the RNA splice sites; and enhancer sequences, such as the SV40 enhancer.

Cloned DNA sequences are introduced into cultured mammalian cells by, for example, calcium phosphate-mediated transfection (Wigler et al., *Cell* 14:725-732, 1978; Corsaro and Pearson, *Somatic Cell Genetics* 7:603-616, 1981; Graham and Van der Eb, *Virology* 52d:456-467, 1973) or electroporation (Neumann et al., *EMBO J.* 1:841-845, 1982). To identify and select cells that express the exogenous DNA, a gene that confers a selectable phenotype (a selectable marker) is generally introduced into cells along with the gene or cDNA of interest. Suitable selectable markers include genes that confer resistance to drugs such as neomycin, hygromycin, and methotrexate. The selectable marker may be an amplifiable selectable marker. A suitable amplifiable selectable marker is a dihydrofolate reductase (DHFR) sequence. Another suitable selectable marker is histidinol. Selectable markers are reviewed by Thilly (*Mammalian Cell Technology*, Butterworth Publishers, Stoneham, Mass., incorporated herein by reference). The person skilled in the art will easily be able to choose suitable selectable markers.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically for 1-2 days, to begin expressing the gene of interest. The medium used to culture the cells may be any conventional medium suitable for growing the host cells, such as minimal or complex media containing appropriate supplements. Suitable media are available from commercial suppliers or may be prepared according to published recipes (e.g., in catalogues of the American Type Culture Collection). The media are prepared using procedures known in the art (see, e.g., references for bacteria and yeast; Bennett, J. W. and LaSure, L., editors, *More Gene Manipulations in Fungi*, Academic Press, CA, 1991). Growth media generally include a carbon source, a nitrogen source, essential amino acids, essential sugars, vitamins, salts, phospholipids, proteins and growth factors. For production of gamma-carboxylated chimeric Factor VII polypeptides, the medium will contain vitamin K, preferably at a concentration of about 0.1 ng/ml to about 20 µg/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of the desired chimeric Factor VII polypeptide.

Suitable mammalian cell lines include the CHO (ATCC CCL 61), COS-1 (ATCC CRL 1650), baby hamster kidney (BHK) and 293 (ATCC CRL 1573; Graham et al., *J. Gen. Virol.* 36:59-72, 1977) cell lines. A suitable BHK cell line is the tk.sup.-ts13 BHK cell line (Waechter and Baserga, *Proc. Natl. Acad. Sci.* USA 79:1106-1110, 1982), hereinafter referred to as BHK 570 cells. The BHK 570 cell line is available from the American Type Culture Collection, 12301 Parklawn Dr., Manassas, Va. 20852, under ATCC accession number CRL 10314. A tk$^{-ts13}$ BHK cell line is also available from the ATCC under accession number CRL 1632. In addition, a number of other cell lines may be used, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (Urlaub and Chasin, Proc. Natl. Acad. Sci. USA 77:4216-4220, 1980).

The chimeric Factor VII polypeptides of the invention may be conjugated to prolong the half-life of the polypeptide in vivo. Such conjugation may decrease renal clearance and increase the amount of Factor VII present in vivo, while decreasing the frequency of administration of the chimeric Factor VII polypeptides. Suitable conjugates and methods of preparing conjugated Factor VII polypeptides are described in U.S. Pat. No. 7,442,524, which is hereby incorporated by reference in its entirety.

Transgenic Animals

Transgenic animal technology may be employed to produce the chimeric Factor VII polypeptides of the invention. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and biochemically well characterized. Furthermore, the major milk proteins are present in milk at high concentrations (typically from about 1 to 15 g/l). The chimeric Factor VII polypeptides of the present invention may also be produced in the urine of a host animal, which has the advantage over production in milk in that both male and female animals produce urine and that there are less proteins in urine than in milk for isolation purposes.

From a commercial point of view when considering use of milk as a source of the chimeric Factor VII polypeptides of the present invention, it is clearly preferable to use as the host a species that has a large milk yield. While smaller animals such as mice and rats can be used (and are preferred at the proof of principle stage), it is preferred to use livestock mammals including, but not limited to, pigs, goats, sheep and cattle. Sheep are particularly suitable due to such factors as the previous history of transgenesis in this species, milk yield, cost and the ready availability of equipment for collecting sheep milk (see, for example, PCT Publication No. WO 88/00239 for a comparison of factors influencing the choice of host species). It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489), beta-lactoglobulin, a-lactalbumin, and whey acidic protein. The beta-lactoglobulin (BLG) promoter is suitable. In the case of the ovine beta-lactoglobulin gene, a region of at least the proximal 406 bp of 5' flanking sequence of the gene will generally be used, although larger portions of the 5' flanking sequence, up to about 5 kbp, are suitable, such as about 4.25 kbp DNA segment encompassing the 5' flanking promoter and non-coding portion of the beta-lactoglobulin gene (see Whitelaw et al., *Biochem. J.* 286: 31-39 (1992)). Similar fragments of promoter DNA from other species are also suitable.

To obtain expression in urine, a urothelium-specific promoter is used. For example, a promoter that drives expression of uroplakin-related genes can be used. (See, e.g., U.S. Pat. No. 6,001,646, which is hereby incorporated by reference in its entirety).

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., *Proc. Natl. Acad. Sci.* USA 85: 836-840 (1988); Palmiter et al., *Proc. Natl. Acad. Sci.* USA 88: 478-482 (1991); Whitelaw et al., *Transgenic Res.* 1: 3-13 (1991); PCT Publication No. WO 89/01343; and PCT Publication No. WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g., the beta-lactoglobulin gene, is preferred. One such region is a DNA segment that provides for intron splicing and RNA polyadenylation from the 3' non-coding region of the ovine beta-lactoglobulin gene. When substituted for the natural 3' non-coding sequences of a gene, this ovine beta-lactoglobulin segment can both enhance and stabilize expression levels of the protein or polypeptide of interest. Within other embodiments, the region surrounding the initiation ATG of the chimeric Factor VII sequence is replaced with corresponding sequences from a milk specific protein gene. Such replacement provides a putative tissue-specific initiation environment to enhance expression. It is convenient to replace the entire chimeric Factor VII pre-pro and 5' non-coding sequences with those of, for example, the BLG gene, although smaller regions may be replaced.

For expression of chimeric FVIIa polypeptides in transgenic animals, a DNA segment encoding chimeric Factor VIIa is operably linked to additional DNA segments required for its expression to produce expression units. Such additional segments include the above-mentioned promoter, as well as sequences that provide for termination of transcription and polyadenylation of mRNA. The expression units will further include a DNA segment encoding a secretory signal sequence operably linked to the segment encoding the chimeric Factor VIIa. The secretory signal sequence may be a native Factor VII secretory signal sequence or may be that of another protein, such as a milk protein (see, for example, von Heijne, *Nucl. Acids Res.* 14: 4683-4690 (1986); and Meade et al., U.S. Pat. No. 4,873,316, which are incorporated herein by reference).

Construction of expression units for use in transgenic animals is conveniently carried out by inserting a chimeric Factor VII sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a chimeric Factor VII polypeptide; thereby creating a gene fusion that includes the expression control sequences of the milk protein gene. In any event, cloning of the expression units in plasmids or other vectors facilitates the amplification of the chimeric Factor VII sequence. Amplification is conveniently carried out in bacterial (e.g., *E. coli*) host cells, thus the vectors will typically include an origin of replication and a selectable marker functional in bacterial host cells. The expression unit is then introduced into fertilized eggs (including early-stage embryos) of the chosen host species. Introduction of heterologous DNA can be accomplished by one of several routes, including microinjection (e.g., U.S. Pat. No. 4,873,191), retroviral infection (Jaenisch, *Science* 240: 1468-1474 (1988)) or site-directed integration using embryonic stem (ES) cells (reviewed by Bradley et al., *Bio/Technology* 10: 534-539 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art (see, for example, Hogan et al., *Manipulating the Mouse Embryo: A Laboratory Manual*, Cold Spring Harbor Laboratory, 1986; Simons et al., *Bio/Technology* 6: 179-183 (1988); Wall et al., *Biol. Reprod.* 32: 645-651 (1985); Buhler et al., *Bio/Technology* 8: 140-143 (1990); Ebert et al., *Bio/Technology* 9: 835-838 (1991); Krimpenfort et al., *Bio/Technology* 9: 844-847 (1991); Wall et al., *J. Cell. Biochem.* 49: 113-120 (1992); U.S. Pat. No. 4,873,191; U.S. Pat. No. 4,873,316; PCT Publication No. WO 88/00239, PCT Publication No. WO 90/05188, PCT Publication No. WO 92/11757; and Great Britain Publication No. GB 87/00458). Techniques for introducing foreign DNA sequences into mammals and their germ cells were originally developed in the mouse (see, e.g., Gordon et al., *Proc. Natl. Acad. Sci. USA* 77: 7380-7384 (1980); Gordon and Ruddle, *Science* 214: 1244-1246 (1981); Palmiter and Brinster, *Cell* 41: 343-345 (1985); Brinster et al., *Proc. Natl. Acad. Sci. USA* 82: 4438-4442 (1985); and Hogan et al.). These techniques were subsequently adapted for use with larger animals, including livestock species (see, e.g., PCT Publication Nos. WO 88/00239, WO 90/05188, and WO 92/11757; and Simons et al., *Bio/Technology* 6: 179-183 (1988)). To summarize, in the most efficient route used to date in the generation of transgenic mice or livestock, several hundred linear molecules of the DNA of interest are injected into one of the pro-nuclei of a fertilized egg according to established techniques. Injection of DNA into the cytoplasm of a zygote can also be employed.

Production in transgenic plants may also be employed. Expression may be generalized or directed to a particular organ, such as a tuber (see, Hiatt, *Nature* 344:469-479 (1990); Edelbaum et al., *J. Interferon Res.* 12:449-453 (1992); Sijmons et al., *Bio/Technology* 8:217-221 (1990); and EP 0 255 378).

Production of the chimeric Factor VII polypeptides of the present invention may also be achieved through in vitro translation, such as for example by rabbit reticulocyte lysate, wheat germ extract and *E. coli* cell free systems. The in vitro translation may also be linked or coupled. Linked in vitro translation is based on transcription with a bacteriophage polymerase followed by translation in the rabbit reticulocyte lysate or wheat germ lysate systems. Coupled in vitro translation is based upon the *E. coli* cell free system.

Recovery and Activation

The chimeric Factor VII polypeptides of the invention are recovered from cell culture medium or milk. The chimeric Factor VII polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*; J.-C. Janson and Lars Ryden, editors, VCH Publishers, New York, 1989). Additional purification may be achieved by conventional chemical purification means, such as high performance liquid chromatography. Other methods of purification, including barium citrate precipitation, are known in the art, and may be applied to the purification of the novel chimeric Factor VII polypeptides described herein (see, for example, Scopes, R., *Protein Purification*, Springer-Verlag, N.Y., 1982).

For therapeutic purposes it is preferred that the chimeric Factor VII polypeptides of the invention are substantially pure. Thus, in one embodiment of the invention the Factor VII variants of the invention are purified to at least about 90 to 95% purity, preferably to at least about 98% purity. Purity may be assessed by e.g., gel electrophoresis, amino-terminal amino acid sequencing and reverse-phase HPLC.

The chimeric Factor VII polypeptide is cleaved at its activation site to convert it to its two-chain form. Activation may be carried out according to procedures known in the art, such as those disclosed by Osterud, et al., *Biochemistry* 11:2853-2857 (1972); Thomas, U.S. Pat. No. 4,456,591; Hedner and Kisiel, *J. Clin. Invest.* 71:1836-1841 (1983); or Kisiel and Fujikawa, *Behring Inst. Mitt.* 73:29-42 (1983). Alternatively, the chimeric Factor VII polypeptide may be activated by concentrating the chimeric Factor VII polypeptide and contacting a positively charged surface or resin, for example, as described by Bjoern et al. (*Research Disclosure*, 269 September 1986, pp. 564-565), Factor VII may be activated by passing it through an ion-exchange chromatography column, such as Mono Q® (Pharmacia fine Chemicals) or the like. The chimeric Factor VII polypeptide may also be activated in solution by obtaining a solution comprising a substantially purified preparation of the chimeric Factor VII polypeptide; adding to the solution an amine compound, $Ca^{2+}$ to a final concentration of about 5 mM to about 50 mM (such as about 10 mM to about 30 mM), and adjusting the final pH of the solution to about 7.2 to 8.6 (such as about 7.6 to about 8.2); incubating the resulting activation mixture at between about 2° C. and about 25° C. for an amount of time sufficient to convert at least 90% of the chimeric FVII polypeptide to chimeric FVIIa polypeptide; and, optionally, isolating the FVIIa from the activation mixture. The resulting activated chimeric Factor VII polypeptide may then be formulated and administered as described below.

Gene Therapy

The chimeric Factor VII polypeptides of the invention may also be used in methods of treating bleeding disorders by way of gene therapy. In this embodiment of the invention, the chimeric Factor VII polypeptides of the invention are encoded by nucleic acid molecules that may be introduced into cells of the subject by ex vivo transfer or by in vivo transfer.

Any of the methods for gene therapy available in the art can be used according to the present invention. Exemplary methods are described below. For general reviews of the methods of gene therapy, see Goldspiel et al., *Clinical Pharmacy* 1993, 12:488-505; Wu and Wu, Biotherapy 1991, 3:87-95; Tolstoshev, *Ann. Rev. Pharmacol. Toxicol.* 1993, 32:573-596; Mulligan, Science 1993, 260:926-932; and Morgan and Anderson, *Ann. Rev. Biochem.* 1993, 62:191-217; May, *TIBTECH* 1993, 11:155-215. Methods commonly known in the art of recombinant DNA technology that can be used are described in Ausubel et al., (eds.), 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al., (eds.), 1994, *Current Protocols in Human Genetics*, John Wiley & Sons, NY; Colosimo et al., *Biotechniques* 2000; 29(2):314-8, 320-2, 324.

The polynucleotides encoding the chimeric Factor VII polypeptides can be inserted into an appropriate cloning vector. Vectors suitable for gene therapy include viruses, such as adenoviruses, adeno-associated virus (AAV), vaccinia, herpesviruses, baculoviruses and retroviruses, parvovirus, lentivirus, bacteriophages, cosmids, plasmids, fungal vectors and other recombination vehicles typically used in the art which have been described for expression in a variety of eukaryotic and prokaryotic hosts, and may be used for gene therapy as well as for simple protein expression.

In one embodiment, the vector is a viral vector. Viral vectors, especially adenoviral vectors can be complexed with a cationic amphiphile, such as a cationic lipid, polyL-lysine (PLL), and diethylaminoethyldextran (DELAE-dextran), which provide increased efficiency of viral infection of target cells (See, e.g., PCT Publication No. PCT/US97/21496 filed Nov. 20, 1997, incorporated herein by reference). Suitable viral vectors for use in the present invention include vectors derived from vaccinia, herpesvirus, AAV and retroviruses. For a review of viral vectors in gene therapy, see Mah et al., *Clin. Pharmacokinet.* 2002; 41(12):901-11; Scott et al., *Neuromuscul. Disord.* 2002; 12 Suppl 1:S23-9.

In one embodiment, a vector is used in which the coding sequences and any other desired sequences are flanked by regions that promote homologous recombination at a desired site in the genome, thus providing for expression of the construct from a nucleic acid molecule that has integrated into the genome (Koller and Smithies, *Proc. Natl. Acad. Sci. USA* 1989, 86:8932-8935; Zijlstra et al., *Nature* 1989, 342:435-438; U.S. Pat. No. 6,244,113 to Zarling et al.; and U.S. Pat. No. 6,200,812 to Pati et al., each of which is incorporated herein in its entirety by reference).

Delivery of the vector into a patient may be either direct, in which case the patient is directly exposed to the vector or a delivery complex, or indirect, in which case, cells are first transformed with the vector in vitro, and then transplanted into the patient. These two approaches are known, respectively, as in vivo and ex vivo gene therapy.

In one embodiment, the vector is directly administered in vivo, where it enters the cells of the subject and mediates expression of the gene. This can be accomplished by any of numerous methods known in the art and discussed above, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell-surface receptors or transfecting agents, encapsulation in biopolymers (e.g., poly-β-1-64-N-acetylglucosamine polysaccharide; see U.S. Pat. No. 5,635,493), encapsulation in liposomes, microparticles, or microcapsules; by administering it in linkage to a peptide or other ligand known to enter the nucleus; or by administering it in linkage to a ligand subject to receptor-mediated endocytosis (see, e.g., Wu and Wu, *J. Biol. Chem.* 1987, 62:4429-4432), etc. In another embodiment, a nucleic acid-ligand complex can be formed in which the ligand comprises a fusogenic viral peptide to disrupt endosomes, allowing the nucleic acid to avoid lysosomal degradation, or cationic 12-mer peptides, e.g., derived from antennapedia, that can be used to transfer therapeutic DNA into cells (Mi et al., *Mol. Therapy* 2000, 2:339-47). In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188). Additionally, a technique referred to as magnetofection may be used to deliver vectors to mammals. This technique associates the vectors with superparamagnetic nanoparticles for delivery under the influence of magnetic fields. This application reduces the delivery time and enhances vector efficacy (Scherer et al., *Gene Therapy* 2002; 9:102-9).

In one embodiment, the nucleic acid can be administered using a lipid carrier. Lipid carriers can be associated with naked nucleic acids (e.g., plasmid DNA) to facilitate passage through cellular membranes. Cationic, anionic, or neutral lipids can be used for this purpose. However, cationic lipids are suitable because they have been shown to associate better with DNA which, generally, has a negative charge. Cationic lipids have also been shown to mediate intracellular delivery of plasmid DNA (Feigner and Ringold, *Nature* 1989; 337: 387). Intravenous injection of cationic lipid-plasmid complexes into mice has been shown to result in expression of the DNA in lung (Brigham et al., *Am. J. Med. Sci.* 1989; 298:278). See also, Osaka et al., *J. Pharm. Sci.* 1996; 85(6):612-618; San et al., *Human Gene Therapy* 1993; 4:781-788; Senior et al., *Biochemica et Biophysica Acta* 1991; 1070:173-179); Kabanov and Kabanov, *Bioconjugate Chem.* 1995; 6:7-20; Liu et al., *Pharmaceut. Res.* 1996; 13; Remy et al., *Bioconjugate Chem.* 1994; 5:647-654; Behr, J-P., *Bioconjugate Chem* 1994; 5:382-389; Wyman et al., *Biochem.* 1997; 36:3008-3017; U.S. Pat. No. 5,939,401 to Marshall et al; U.S. Pat. No. 6,331,524 to Scheule et al.

Representative cationic lipids include those disclosed, for example, in U.S. Pat. No. 5,283,185; and e.g., U.S. Pat. No. 5,767,099, the disclosures of which are incorporated herein by reference. In one embodiment, the cationic lipid is $N_4$-spermine cholesteryl carbamate (GL-67) disclosed in U.S. Pat. No. 5,767,099. Additional suitable lipids include $N_4$-spermidine cholestryl carbamate (GL-53) and 1-($N_4$-spermine)-2,3-dilaurylglycerol carbamate (GL-89).

For in vivo administration of viral vectors, an appropriate immunosuppressive treatment can be employed in conjunction with the viral vector, e.g., adenovirus vector, to avoid immuno-deactivation of the viral vector and transfected cells. For example, immunosuppressive cytokines, such as interleukin-12 (IL-12), interferon-.gamma. (IFN-.gamma.), or anti-CD4 antibody, can be administered to block humoral or cellular immune responses to the viral vectors. In that regard, it is advantageous to employ a viral vector that is engineered to express a minimal number of antigens.

Somatic cells may be engineered ex vivo with a construct encoding a chimeric Factor VII polypeptide of the invention using any of the methods described above, and re-implanted into an individual. This method is described generally in PCT Publication No. WO 93/09222 to Selden et al. In addition, this technology is used in Cell Based Delivery's proprietary ImPACT technology, described in Payumo et al., *Clin. Orthopaed. and Related Res.* 2002; 403S: S228-S242. In such a gene therapy system, somatic cells (e.g., fibroblasts, hepatocytes, or endothelial cells) are removed from the patient, cultured in vitro, transfected with the gene(s) of therapeutic interest, characterized, and reintroduced into the patient. Both primary cells (derived from an individual or tissue and engineered prior to passaging), and secondary cells (passaged in vitro prior to introduction in vivo) can be used, as well as immortalized cell lines known in the art. Somatic cells useful for the methods of the present invention include but are not limited to somatic cells, such as fibroblasts, keratinocytes, epithelial cells, endothelial cells, hepatocytes, formed elements of the blood, muscle cells, other somatic cells that can be cultured, and somatic cell precursors. In one embodiment, the cells are hepatocytes.

Constructs that include the polynucleotide encoding the chimeric FVIIa polypeptides of the invention and, optionally, nucleic acids encoding a selectable marker, along with additional sequences necessary for expression of the chimeric FVIIa in recipient primary or secondary cells, are used to transfect primary or secondary cells in which the encoded product is to be produced. Such constructs include but are not limited to infectious vectors, such as retroviral, herpes, adenovirus, adeno-associated virus, mumps and poliovirus vectors, can be used for this purpose.

Transdermal delivery is especially suited for indirect transfer using cell types of the epidermis including keratinocytes, melanocytes, and dendritic cells (Pfutzner et al., Expert Opin. Investig. Drugs 2000; 9:2069-83).

In one embodiment, the vector for gene therapy is a single-stranded self complementary adeno-associated virus. Additionally, this self complementary adeno-associated virus may contain the small transhyretin promoter-enhancer, introns from the mouse minute virus and the polyadenylation signal from bovine growth hormone. The vector may also contain the RKRRKR sequence described by Margaritis et al. that causes the Factor VII to be secreted in the active form, i.e., Factor VIIa. (Margaritis et al., *J. Clin. Invest.,* 2004; 113: 1025-31).

Administration and Pharmaceutical Compositions

The chimeric Factor VII polypeptides according to the present invention may be used to control bleeding disorders which have several causes such as clotting factor deficiencies (e.g., hemophilia A and B or deficiency of coagulation factors XI or VII) or clotting factor inhibitors, or they may be used to control excessive bleeding occurring in subjects with a normally functioning blood clotting cascade (no clotting factor deficiencies or inhibitors against any of the coagulation factors). The bleedings may be caused by a defective platelet function, thrombocytopenia or von Willebrand's disease. They may also be seen in subjects in whom an increased fibrinolytic activity has been induced by various stimuli.

In subjects who experience extensive tissue damage in association with surgery or trauma, the haemostatic mechanism may be overwhelmed by the demand of immediate hemostasis and they may develop bleedings in spite of a normal haemostatic mechanism. Achieving satisfactory hemostasis is also a problem when bleedings occur in organs such as the brain, inner ear region and eyes and may also be a problem in cases of diffuse bleedings (hemorrhagic gastritis and profuse uterine bleeding) when it is difficult to identify the source. The same problem may arise in the process of taking biopsies from various organs (liver, lung, tumor tissue, gastrointestinal tract) as well as in laparoscopic surgery. These situations share the difficulty of providing hemostasis by surgical techniques (sutures, clips, etc.). Acute and profuse bleedings may also occur in subjects on anticoagulant therapy in whom a defective hemostasis has been induced by the therapy given. Such subjects may need surgical interventions in case the anticoagulant effect has to be counteracted rapidly. Another situation that may cause problems in the case of unsatisfactory hemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

For treatment in connection with deliberate interventions, the chimeric Factor VII polypeptides of the invention will typically be administered within about 24 hours prior to performing the intervention, and for as much as 7 days or more thereafter. Administration as a coagulant can be by a variety of routes as described herein.

The dose of the chimeric Factor VII polypeptides ranges from about 0.05 mg/day to about 500 mg/day, preferably from about 1 mg/day to about 200 mg/day, and more preferably from about 10 mg/day to about 175 mg/day for a 70 kg subject as loading and maintenance doses, depending on the weight of the subject and the severity of the condition. One of skill in the art would be able to determine the optimal dose for a given subject and a given condition.

The pharmaceutical compositions are primarily intended for parenteral administration for prophylactic and/or therapeutic treatment. Preferably, the pharmaceutical compositions are administered parenterally, i.e., intravenously, subcutaneously, or intramuscularly, or it may be administered by continuous or pulsatile infusion. Alternatively, the pharmaceutical compositions may be formulated for administration in various ways, including, but not limited to, orally, subcutaneously, intravenously, intracerebrally, intranasally, transdermally, intraperitoneally, intramuscularly, intrapulmonary, vaginally, rectally, intraocularly, or in any other acceptable manner.

The compositions for parenteral administration comprise the chimeric Factor VII polypeptide of the invention in combination with, preferably dissolved in, a pharmaceutically acceptable carrier, preferably an aqueous carrier. A variety of aqueous carriers may be used, such as water, buffered water, 0.4% saline, 0.3% glycine and the like. The chimeric Factor VII polypeptides of the invention may also be formulated with compositions that prolong stability and storage, such as methionine and sucrose. The chimeric Factor VII polypeptides of the invention can also be formulated into liposome preparations for delivery or targeting to the sites of injury. Liposome preparations are generally described in, e.g., U.S. Pat. Nos. 4,837,028, 4,501,728, and 4,975,282. The compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. The compositions may also contain preservatives, isotonifiers, non-ionic surfactants or detergents, antioxidants and/or other miscellaneous additives.

The concentration of chimeric Factor VII polypeptide in these formulations can vary widely, i.e., from less than about 0.5% by weight, usually at or at least about 1% by weight to as much as about 15 or 20% by weight and will be selected primarily by fluid volumes, viscosities, etc., in accordance with the particular mode of administration selected. Thus, a typical pharmaceutical composition for intravenous infusion could be made up to contain 250 ml of sterile Ringer's solution and 10 mg of the chimeric Factor VII polypeptide. Actual methods for preparing parenterally administrable compositions will be known or apparent to those skilled in the art and are described in more detail in, for example, *Remington's Pharmaceutical Sciences,* 18th ed., Mack Publishing Company, Easton, Pa. (1990).

The compositions containing the chimeric Factor VII polypeptide of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as a "therapeutically effective amount." As will be understood by the person skilled in the art amounts effective for this purpose will depend on the severity of the disease or injury as well as the weight and general state of the subject. In general, however, the effective amount will range from about 0.05 mg up to about 500 mg of the chimeric Factor VII polypeptide per day for a 70 kg subject, with dosages of from about 1.0 mg to about 200 mg of the chimeric Factor VII polypeptide per day being more commonly used.

It must be kept in mind that the materials of the present invention may generally be employed in serious disease or injury states, that is, life threatening or potentially life threatening situations. In such cases, in view of the minimization of extraneous substances and general lack of immunogenicity of human Factor VII in humans, it is possible and may be felt desirable by the treating physician to administer a substantial excess of these chimeric Factor VII polypeptide compositions.

In prophylactic applications, compositions containing the chimeric Factor VII polypeptide of the invention are administered to a subject susceptible to or otherwise at risk of a disease state or injury to enhance the subject's own coagulative capability. Such an amount is defined to be a "prophylactically effective dose." In prophylactic applications, the precise amounts once again depend on the subject's state of health and weight, but the dose generally ranges from about 0.05 mg to about 500 mg per day for a 70-kilogram subject, more commonly from about 1.0 mg to about 200 mg per day for a 70-kilogram subject.

Single or multiple administrations of the compositions can be carried out with dose levels and patterns being selected by the treating physician. For ambulatory subjects requiring daily maintenance levels, the chimeric Factor VII polypeptides may be administered by continuous infusion using e.g., a portable pump system.

The chimeric Factor VII polypeptides of the present invention may also be formulated in sustained, or extended release formulations. Methods of formulating sustained, or extended release compositions are known in the art and include, but are not limited to, semi-permeable matrices of solid hydrophobic particles containing the polypeptide.

Local delivery of the chimeric Factor VIIa polypeptides of the present invention, such as, for example, topical application may be carried out, for example, by means of a spray, perfusion, double balloon catheters, stent, incorporated into vascular grafts or stents, hydrogels used to coat balloon catheters, or other well established methods. In any event, the pharmaceutical compositions should provide a quantity of Factor VII variant sufficient to effectively treat the subject.

The following examples have been included to illustrate the invention. Certain aspects of the following examples are described in terms of techniques and procedures found or contemplated by the present co-inventors to work well in the practice of the invention. In light of the present disclosure and the general level of skill in the art, those of skill will appreciate that the following examples are intended to be exemplary only and that numerous changes, modifications, and alterations may be employed without departing from the scope of the invention.

EXAMPLES

Example I

Construction and Expression of Chimeric Factor VIIa Polypeptides

The cDNA of both human Factor VII and human Factor IX were obtained and the following unique restriction sites were introduced to facilitate domain exchange:

BstEII site at the 5' end of EGF-1 domain (residues 47-49 of Factor VII; residues 48-50 of Factor IX);

SacI site is at the junction of the EGF-1 and EGF-2 domains (residues 82-83 of Factor VII; residues 83-84 of Factor IX);

NotI site is at the 3' end of the EGF-2 domain (residues 135-137 of Factor VII; residues 132-134 of Factor IX.

Various chimeras were constructed using these restriction sites to exchange domains between Factor VII and Factor IX and are depicted in FIG. 1. The same, or similar restriction sites can be used to exchange domains between Factor VII and Protein S.

The amino acid sequence of the resulting chimeras are set forth in SEQ ID NO:1 (Factor IX signal, propeptide, GLA and EGF1 domains, with Factor VII EGF2 and catalytic domains) and SEQ ID NO:2 (Factor IX signal and propeptide domains, Protein S GLA domain, Factor IX EGF1 domain, with Factor VII EGF2 and catalytic domains). A selection of these recombinant DNAs were subcloned into the expression vector pCMV5 for mammalian cell transfection.

The resulting recombinant constructs were then co-transfected with pSV2neo and pCMVhGC into the 293 human kidney cell line (ATCC CRL 1573). A clone expressing a high level of each construct was selected and screened as previously described (Toomey et al., 1991, J. Biol. Chem., 266: 19198-19202). Each screened clone was expanded to 900 cm$^2$ roller bottles for large scale production and recombinant proteins were purified by a pseudo-affinity chromatographic method using Fast Flow Q-Sepharose and elution with a calcium gradient, followed by a NaCl gradient.

Example II

Thrombin Generation of Factor VIIa Polypeptides

The thrombin generation of Factor VIIa was determined using an in vitro model of hemophilia. Monocytes were used as a source of tissue factor and combined with unactivated platelets and synthetic plasma containing plasma concentrations of Factors V, VII, IX, VIII, and XI, and plasma concentrations of antithrombin and TFPI. Hemophilic conditions were created by omitting factors VIII and IX.

Monocytes were prepared by drawing 4 ml of blood from a healthy individual and placing in a sodium citrate tube. The blood was carefully layered on top of 3 ml of Accu-Prep™ Lymphocyte separation medium (Accurate Chemicals, NY, USA) in a 15 ml conical tube and centrifuged at 1500 rpm for 30 minutes. The mononuclear layer was then removed and added to an equal volume of Versene (Lineberger Tissue Culture) at 4° C. and centrifuged at 800 rpm for 10 minutes. The resulting pellet was resuspended in 5 ml of Versene at 4° C. and centrifuged at 800 rpm for 10 minutes. The resulting pellet was resuspended in 4 ml of macrophage SFM media (Life Technologies, CA, USA), supplemented with 500 ng/ml of lipopolysaccharide (LPS) (Sigma-Aldrich, MO, USA) and cells were plated at 200 μl/well of a 96-well plate. The plate was incubated at 37° C., 5% $CO_2$ for two hours and then washed three times with macrophage SFM media and then incubated overnight.

Platelets were prepared by drawing 4 ml of blood from a healthy individual and placing in a sodium citrate tube. The blood was carefully layered on top of 5 ml of Accu-Prep™ Lymphocyte separation medium (Accurate Chemicals, NY, USA) in a 15 ml conical tube and centrifuged at 1500 rpm for 30 minutes. The platelet layer was then removed and added to an equal volume of citrate-glucose-saline with 10 μg/ml of prostaglandin $E_1$ (PGE1) (Sigma-Aldrich, MO, USA) and centrifuged at 800 rpm for 10 minutes. The resulting pellet was discarded and the platelets were isolated from plasma proteins by Sepharose gel filtration in calcium free Tyrodes buffer supplemented with 1 mg/ml ovalbumin. The recovered platelets were stored at 37° C.

Synthetic plasma for the in vitro assay that mimics hemophilia was generated by using Factor XI C-1-esterase inhibitor at a concentration of 5 μg/ml with the addition after 1 hour incubation with the previously prepared monocytes of 200 μg/ml antithrombin, 0.07 μg/ml of TFPI, 100 mg/ml of prothrombin, 8 μg/ml of Factor X and 0.5 μg/ml of Factor VII. Following an overnight incubation, Factor V was added at a concentration of 7 μg/ml. For normal conditions, Factor IX was added after the 1 hour incubation at a concentration of 4 μg/ml and following the overnight incubation, Factor VIII was added at 1 U/ml.

260 μl of platelets were added to the above synthetic plasma solutions and the resulting suspension was added to the monocytes to start the reaction. At timed intervals 10 μl samples were removed and added to 90 μl of thrombin assay buffer containing 1 mM EDTA and 0.5 mM Gly-Pro-Arg-pNA (Centerchem Inc., CT, USA). 100 μl of 50% acetic acid was added to stop synthetic substrate cleavage and the OD was measured at 405 nm. Thrombin concentration was determined using the following formula:

[thrombin]=dilution×((A405-background)/(stop-start))/(conversion factor)

wherein the conversion factor is 1 nM thrombin gives a rate of 0.0117 OD/min at 405 nm.

Figure 2:
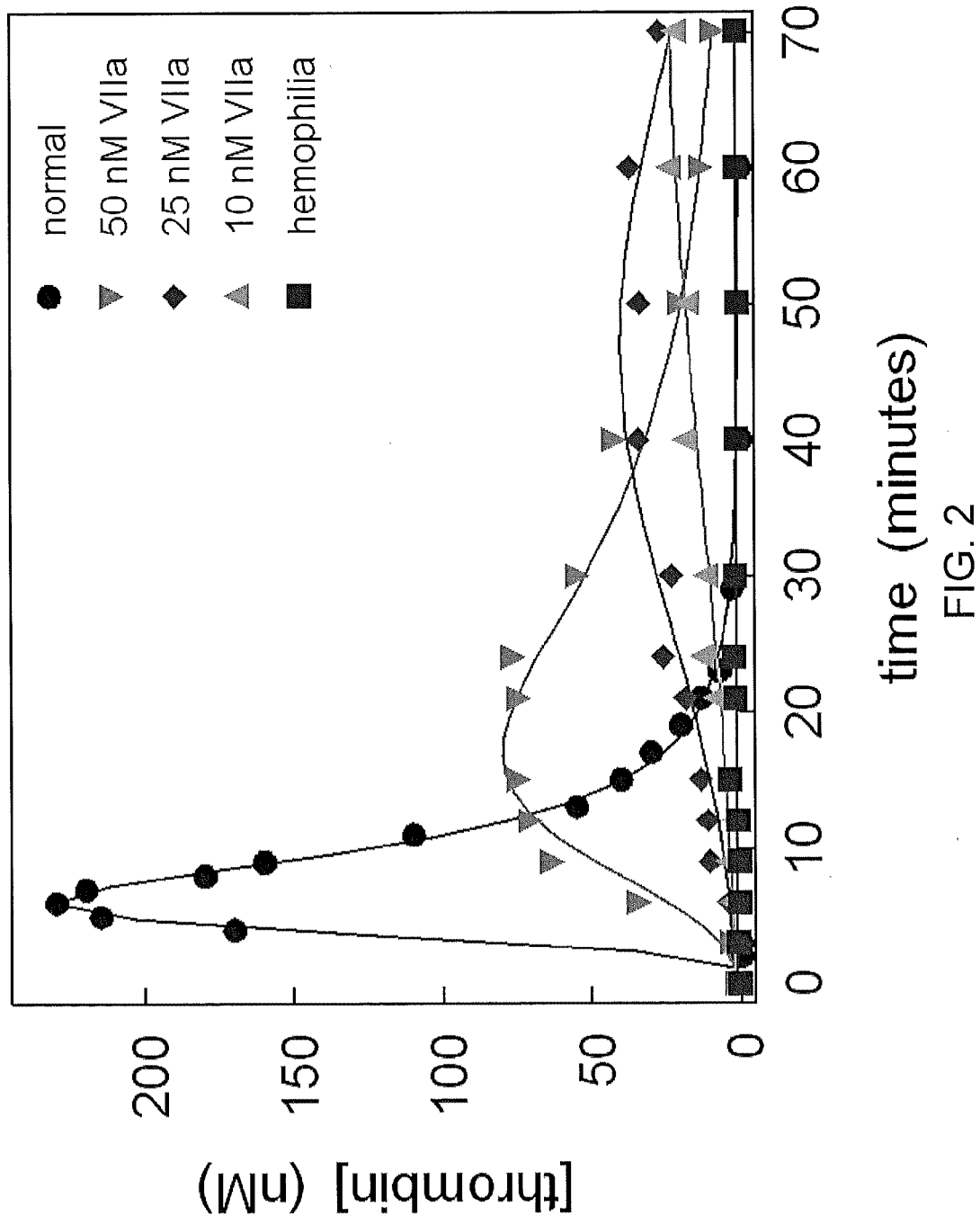
FIG. 2 shows the thrombin generation (nM) in normal conditions and hemophilic conditions (removal of Factor IX and Factor VIII) in a cell based model system of hemophilia for varying concentrations of wild-type Factor VIIa.

Thrombin generation in normal conditions (Factors VIII and IX included) shows peak thrombin production with a short lag phase (FIG. 2). Increasing concentrations of wild-type Factor VIIa improved thrombin production in the hemophilic condition. (FIG. 2).

Example III

Thrombin Generation of Chimeric Factor VIIa Polypeptides

Figure 3:
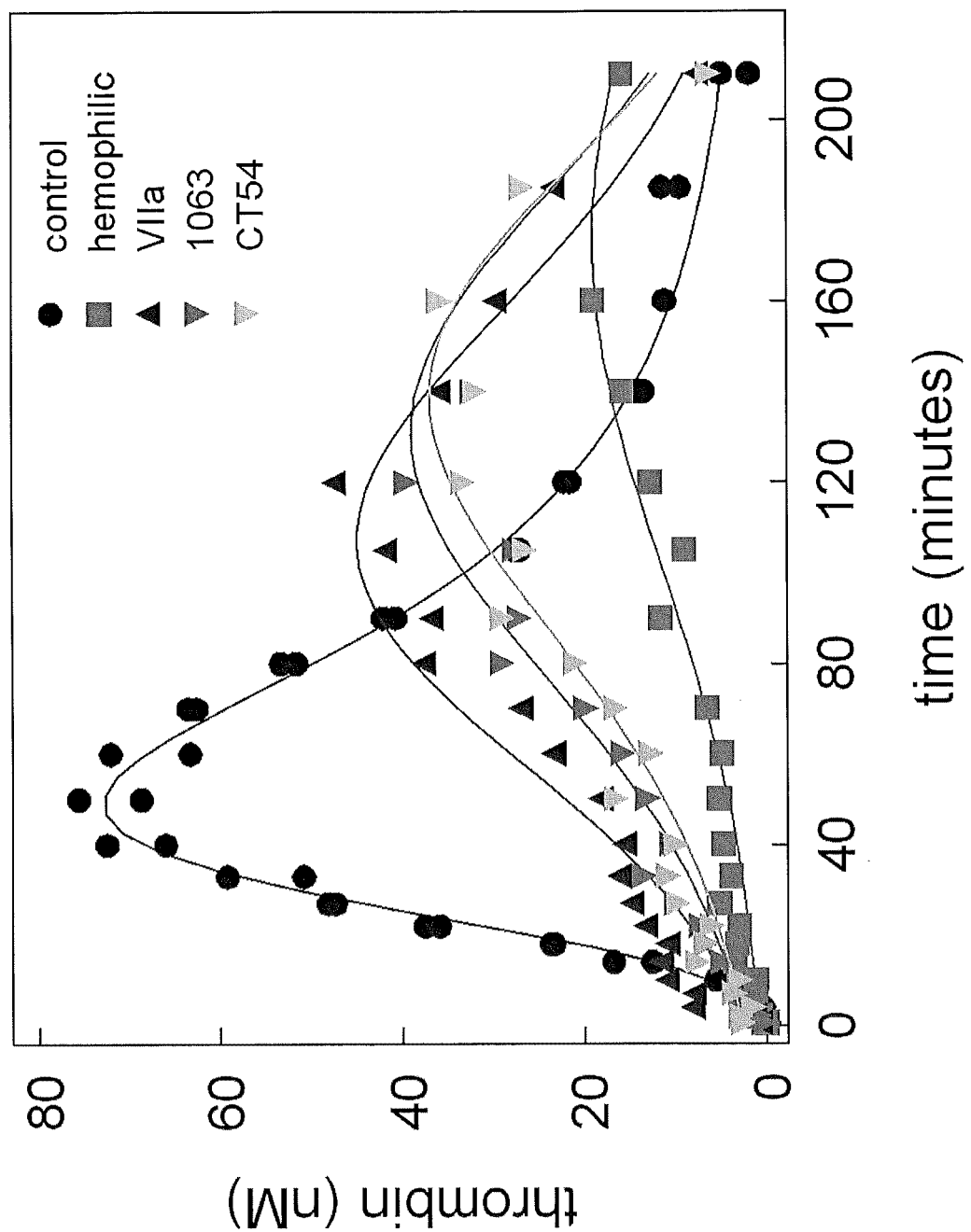
FIG. 3 shows the thrombin generation (nM) in normal conditions and hemophilic conditions (removal of Factor IX and Factor VIII) in a cell based model system of hemophilia with administration of 50 nM wild-type Factor VIIa, or 10 nM chimeric Factor VIIa.

The thrombin generation of the chimeric proteins produced in Example I was determined using an in vitro model of hemophilia described in Example II. The addition of 10 nM of a chimeric Factor VIIa containing the EGF-2 and catalytic domains of Factor VII and the GLA and EGF-1 domains of Factor IX, or a chimeric Factor VIIa containing the GLA, EGF-2 and catalytic domains of Factor VII and the EGF-1 domain of Factor IX had a similar activity to 50 nM of wild-type Factor VIIa. (FIG. 3).

Figure 4:
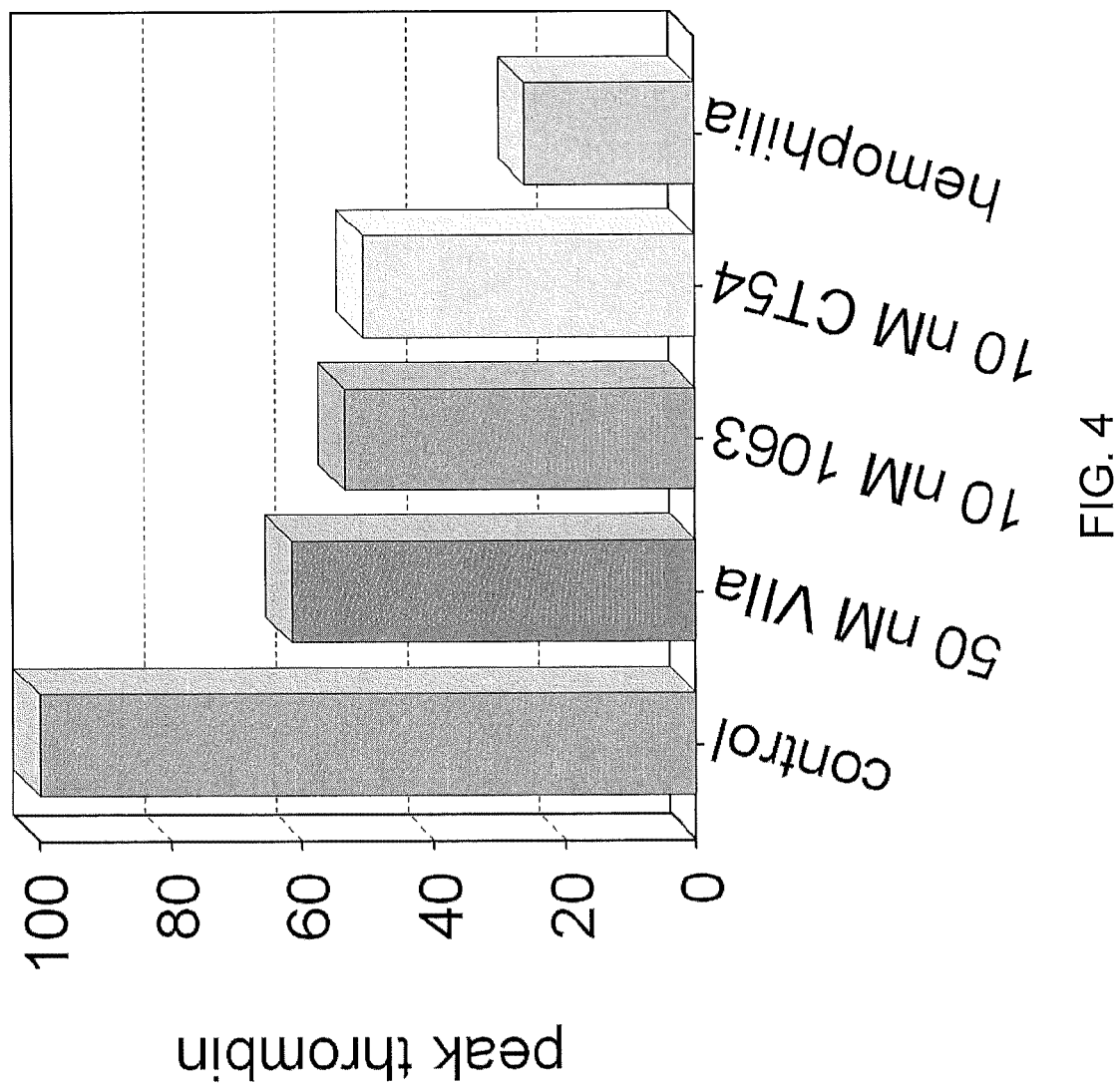
FIG. 4 shows the peak thrombin, relative to the control value, produced in a cell based model system of hemophilia following administration of 50 nM wild-type Factor VIIa, or 10 nM chimeric Factor VIIa.

Looking at peak thrombin production in relation to the control, neither wild-type Factor VIIa, nor the chimeric Factor VIIa polypeptides tested restored peak thrombin production to the level of the control. However, 10 nM of a chimeric Factor VIIa containing the EGF-2 and catalytic domains of Factor VII and the GLA and EGF-1 domains of Factor IX, or a chimeric Factor VIIa containing the GLA, EGF-2 and catalytic domains of Factor VII and the EGF-1 domain of Factor IX restored peak thrombin production to a level similar to that produced by 50 nM of wild-type Factor VIIa. (FIG. 4).

Example IV

Clotting Assay of Chimeric Factor VIIa Polypeptides

The clotting activity of the chimeric Factor VIIa polypeptides was assessed in vivo, in a clotting assay, as described by Buyue, Y., et al., 2008, *Blood*, 112:3234-3241. Briefly, Factor VII was administered to a hemophilia B mouse (2 mg/kg of NovoSeven®, 2 mg/kg of a chimeric Factor VIIa containing the GLA and EGF-1 domains of Factor IX and the EGF-2 and catalytic domains of Factor VIIa, or 1.4 mg/kg of a chimeric Factor VIIa containing the GLA domain of Protein S, the EGF-1 domain of Factor IX and the EGF-2 and catalytic domains of Factor VIIa), through a catheter inserted into a vein in the leg. A wild-type mouse was used as a control. The mice were anesthetized and the saphenous vein of the other leg was transected by pushing a small gauge needle through it. The distal portion is then cut by inserting the tip of a pair of scissors into the vein and snipping to create a small cup. A clot is formed and the time until bleeding stops was recorded. The clot was then removed using a 30 gauge needle and the time until bleeding stops was again recorded. This process was repeated for 30 minutes. The number of clots was recorded as the number of disruptions. The times recorded were averaged and recorded as an average time. The experiment was conducted on one mouse for the wild-type mouse and the chimeric FactorVIIa containing the GLA domain of Protein S, the EGF-1 domain of Factor IX and the EGF-2 and catalytic domains of Factor VIIa. For the chimeric Factor VIIa containing the GLA and EGF-1 domains of Factor IX and the EGF-2 and catalytic domains of Factor VIIa the experiment was conducted on two hemophilia B mice with the same results. For the hemophilia B mouse that was not administered any Factor VII, the 0.25 disruptions recorded in Table 1 below indicate that only one out of four mice did not bleed out with the initial injury.

TABLE 1

|  | Hemo-philia B | NovoSeven® | C1 (1063) | C2 | WT Mouse |
|---|---|---|---|---|---|
| Disruptions | 0.25 | 20 | 29 | 13 | 25 |
| Average time (sec) | 1712 | 71 | 51 | 125 | 54 |

Figure 5:
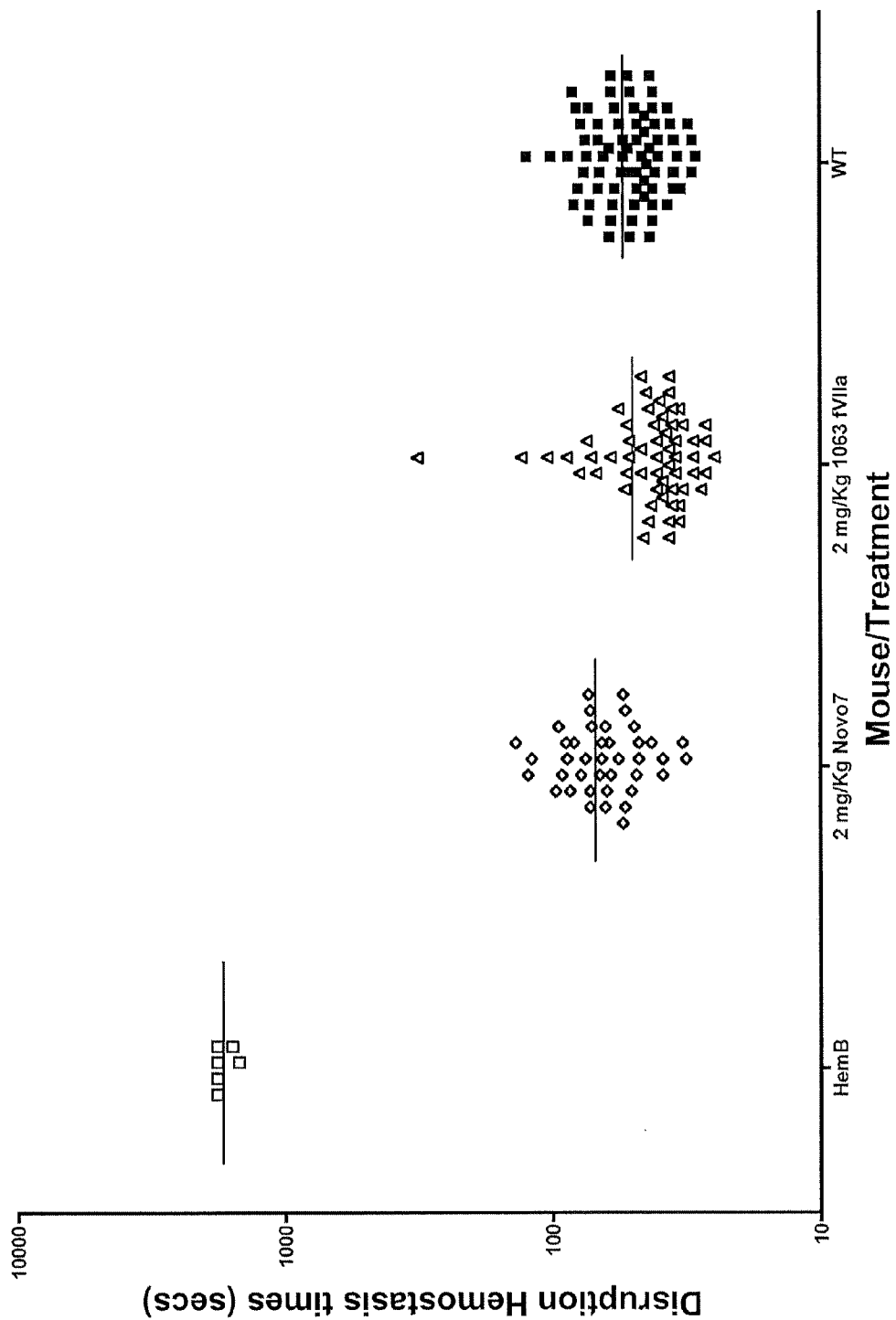
FIG. 5 shows the disruption hemostasis time in a clotting assay for a hemophilia B mouse with no treatment, a hemophilia B mouse administered with 2 mg/kg of NovoSeven®, a hemophilia B mouse administered with 2 mg/kg of a chimeric FVIIa molecule and a wild-type mouse with no treatment.

The experiment was repeated with one hemophilia B mouse with no treatment, one hemophilia B mouse administered 2 mg/kg of NovoSeven®, one hemophilia B mouse administered 2 mg/kg of a chimeric Factor VIIa containing the GLA and EGF-1 domains of Factor IX and the EGF-2 and catalytic domains of Factor VIIa and one wild-type mouse with no treatment. The hemophilia B mouse administered the 2 mg/kg of chimeric Factor VIIa containing the GLA and EGF-1 domains of Factor IX and the EGF-2 and catalytic domains of Factor VIIa had a shorter average time to cessation of bleeding than the hemophilia B mouse administered 2 mg/kg of NovoSeven® and the wild-type mouse. (FIG. 5).

Example V

Thrombogenicity of Chimeric Factor VIIa Polypeptides

Thrombogenicity of the chimeric Factor VIIa polypeptides of the invention can be tested in a mouse model that expresses high levels of these proteins. Recently, it has been shown that 50% of mice expressing greater than 2 µg/ml recombinant wild type mouse factor VIIa died from thromboses within 16 months. Hemophilia B mice expressing similar levels of factor VIIa had the same mortality rates and that when the mice were back-crossed into the C57BL/6J mouse strain, thromboses occurred much earlier (<4 months). (Aljamali M N, et al. *J Clin Invest.* 2008; 118:1825-1834).

A hemophilia B mouse (strain C57BL/6J) expressing 2-10 µg or more of the chimeric polypeptides can be produced and if expression of the chimeric Factor VII polypeptides cause thromboses then these mice should develop them early on (<4 months).

The mouse strain can be developed by using a new self complementary adeno associated vector (AAV) developed by Dr. Paul Monahan of the Gene Therapy Center at UNC. (Wu Z, et al. *Mol Ther.* 2008; 16:280-289). This vector contains the small transhyretin promoter-enhancer (TTR promoter), introns from the minute virus of mouse, the MVM and the bovine growth hormone pA signal. It has been shown that injection of $1\times10^{11}$ vector genomes, based on this vector, into the portal vein resulted in sustained expression of Factor IX of 7 µg per ml within 8 weeks of infection. (Wu Z, et al. *Mol Ther.* 2008; 16:280-289).

The cDNA of both mouse and human factor VIIa, as well as the chimeric Factor VII polypeptides of the invention may be used to assess thrombogenicity. The RKRRKR (SEQ ID NO:21) sequence described by Margaritis et al. that causes the Factor VII to be secreted in the active form, i.e., Factor VIIa. (Margaritis et al., *J. Clin. Invest.*, 2004; 113:1025-31) can also be used.

To test this hypothesis, wild-type and chimeric Factor VII mouse polypeptides can be generated. It has been reported that mouse tissue factor does not react with human Factor VII, so mouse polypeptides are used to demonstrate that tissue factor is irrelevant to the action of administered Factor VIIa in trauma but is related to thrombosis. The mouse polypeptides that can be used to test this hypothesis include a wild-type mouse Factor VII (SEQ ID NO:3), a wild-type mouse Factor VII with an RKRRKR sequence to cause the polypeptide to be secreted in the two-chain, active form (FVIIa) (SEQ ID NO:4), a mouse Factor IX signal, propeptide, GLA and EGF1 domains, with Factor VII EGF2 and catalytic domains and an RKRRKR sequence (SEQ ID NO:5) and a mouse Factor IX signal and propeptide domains, Protein S GLA domain, Factor IX EGF1 domain, with Factor VII EGF2 and catalytic domains and an RKRRKR sequence (SEQ ID NO:6). The chimeric mouse Factor VII polypeptides (SEQ ID NOS: 5 and 6) will have a reduced affinity for tissue factor (perhaps by as much as 100 fold lower when compared to the wild-type FVII molecule) and this should be sufficient to prevent unwanted thromboses.

The chimeric Factor VII polypeptides may also be additionally modified to further reduce the affinity for tissue factor. An example of such a mutation is to change the methionine at residue 306 to alanine. Other modifications of the chimeric Factor VII polypeptides may be included that result in a higher specific activity of Factor VIIa. Examples of such modifications include the following equivalent to residues 158, 296 and 298 of the human sequence: V158D, E296V and M298Q.

The wild-type and chimeric mouse Factor VII polypeptides described above can be constructed by using mouse Factor VII cDNA as a template and using oligonucleotide primers to amplify the various domains and then inserting the constructs into a pSC-TTR-mvm vector, the construction of which is described in Wu et al., Molecular Therapy, 2008; 16:280-289. Specifically, the wild-type mouse Factor VII can be amplified from mouse Factor VII cDNA using the following primers: 5'-TGAGGATCCCCACCATGGTTCCACAG-GCGCATGGGCT-3' (SEQ ID NO:7) and 5'-TTCCCCAG-CATGCCTACAGTAGTGGGAGTCGGAAAAC-3' (SEQ ID NO:8). The amplified fragment can then be digested with BamHI/SphI and inserted into the pSC-TTR-mvm vector between the BglII/SphI sites. Subsequently, the BGH polyadenylation sequence can be inserted into the resulting vector at the SphI site.

The wild-type mouse Factor VII construct with the RKRRKR sequence can be constructed in a similar fashion. Specifically, the wild-type mouse Factor VII with the RKRRKR sequence can be amplified from mouse Factor VII cDNA using the following primers:

5'-TGAGGATCCCCACCATGGTTCCACAG-GCGCATGGGCT-3' (SEQ ID NO:7) and 5'-ACAAT-GCGTTTTCGCCGCTTACGGCGGCCTTG-GCGGCTGCTGGAGT-3' (SEQ ID NO:9), to generate a first fragment; and, 5'-TTCCCCAGCATGCCTACAGTAGTGG-GAGTCGGAAAAC-3' (SEQ ID NO: 8) and 5'-GCCGCCG-TAAGCGGCGAAAACGCATTGTGGGAG-GCAACGTGTGCCC-3' (SEQ ID NO:10) to generate a second fragment. An overlapping PCR is then performed using these two fragments as template and the following primers:

5'-TGAGGATCCCCACCATGGTTCCACAG-GCGCATGGGCT-3' (SEQ ID NO:7) and 5'-TTCCCCAG-CATGCCTACAGTAGTGGGAGTCGGAAAAC-3' (SEQ ID NO:8). The resulting amplified fragment can then be digested with BamHI/SphI and inserted into the pSC-TTR-mvm vector between the BglII/SphI sites. Subsequently, the BGH polyadenylation sequence can be inserted into the resulting vector at the SphI site.

The construct containing the mouse Factor IX signal, propeptide, GLA and EGF1 domains, with Factor VII EGF2 and catalytic domains and an RKRRKR sequence (SEQ ID NO:5) is similarly constructed. Specifically, a first fragment is generated using mouse FactorIX cDNA as a template and the following primers:

5'-AGGCCTGAAGATCTCCACCATGAAGCAC-CTGAACACCGTC-3' (SEQ ID NO:11) and

5'-GATCAGCTGCTCATTCTTGCTTTTTTCA-CAGTTCCTTCCTTCAAATC-3' (SEQ ID NO:12). A second fragment is generated using mouse Factor VII as a template and the following primers:

5'-GATTTGAAGGAAGGAACTGTGAAAAAAG-CAAGAATGAGCAGCTGATC-3' (SEQ ID NO:13)

and 5'-ACAATGCGTTTTCGCCGCTTACGGCGGC-CTTGGCGGCTGCTGGAGT-3' (SEQ ID NO:9).

A third fragment can be generated using mouse Factor VII as a template and the following primers: 5'-TTCCCCAG-CATGCCTACAGTAGTGGGAGTCGGAAAAC-3' (SEQ ID NO:8) and
5'-GCCGCCGTAAGCGGCGAAAACGCAT-TGTGGGAGGCAACGTGTGCCC-3' (SEQ ID NO:10). An overlapping PCR can then be performed using these three fragments as template and primers
5'-AGGCCTGAAGATCTCCACCATGAAGCAC-CTGAACACCGTC-3' (SEQ ID NO:11) and 5'-TTC-CCCAGCATGCCTACAGTAGTGGGAGTCGGAAAAC-3' (SEQ ID NO:8). The resulting amplified fragment is then digested with BamHI/SphI and inserted into the pSC-TTR-mvm vector between the BglII/SphI sites. Subsequently, the BGH polyadenylation sequence is inserted into the resulting vector at the SphI site.

A similar process can be used to generate the construct containing the mouse Factor IX signal and propeptide domains, Protein S GLA domain, Factor IX EGF1 domain, with Factor VII EGF2 and catalytic domains and an RKRRKR sequence (SEQ ID NO: 6). Specifically, a first fragment can be generated using mouse Factor IX cDNA and the following primers: 5'-AGGCCTGAAGATCTCCAC-CATGAAGCACCTGAACACCGTC-3' (SEQ ID NO:11) and
5'-GTTTCTTCGAACAAGG-TATTTGCTCTCTTTGGACGGGTAAGAATTTTG-3' (SEQ ID NO:14). A second fragment can be generated using mouse Protein S as a template and the following primers:
5'-CAAAATTCTTACCCGTCCAAAGAGAG-CAAATACCTTGTTCGAAGAAAC-3' (SEQ ID NO:15) and 5'-GATCTCCATCAACATACTGCT-TATAAAAATAATCCGTCTCGGGATT-3' (SEQ ID NO:16). A third fragment can be generated using the vector with the mouse Factor IX signal, propeptide, GLA and EGF1 domains, with Factor VII EGF2 and catalytic domains and an RKRRKR sequence as a template and the following primers:
5'-AATCCCGAGACGGATTATTTTTATAAG-CAGTATGTTGATGGAGATC-3' (SEQ ID NO:17) and 5'-TTCCCCAGCATGCCTACAGTAGTGG-GAGTCGGAAAAC-3' (SEQ ID NO:8). An overlapping PCR is then performed using these three fragments as template and primers:

5'-AGGCCTGAAGATCTCCACCATGAAGCAC-CTGAACACCGTC-3' (SEQ ID NO:11) and 5'-TTC-CCCAGCATGCCTACAGTAGTGGGAGTCGGAAAAC-3' (SEQ ID NO:8). The resulting amplified fragment is then digested with BamHI/SphI and inserted into the pSC-TTR-mvm vector between the BglII/SphI sites. Subsequently, the BGH polyadenylation sequence can be inserted into the resulting vector at the SphI site.

The wild-type mouse Factor VII (SEQ ID NO:3) and wild-type mouse Factor VII with the RKRRKR sequence (SEQ ID NO:4) vector constructs were each injected into two male hemophilia B mice of matched age ($5\times10^{11}$ vector genomes per mouse). The mouse Factor IX signal, propeptide, GLA and EGF 1 domains, with Factor VII EGF2 and catalytic domains and an RKRRKR sequence (SEQ ID NO:5) and mouse Factor IX signal and propeptide domains, Protein S GLA domain, Factor IX EGF1 domain, with Factor VII EGF2 and catalytic domains and an RKRRKR sequence (SEQ ID NO:6) vector constructs were each injected into three male hemophilia B mice of matched age ($5\times10^{11}$ vector genomes per mouse). Approximately three weeks post-injection, all mice injected with wild-type mouse Factor VII with the RKRRKR sequence (SEQ ID NO:4) died. The mice injected with either mouse Factor IX signal, propeptide, GLA and EGF1 domains, with Factor VII EGF2 and catalytic domains and an RKRRKR sequence (SEQ ID NO:5), or mouse Factor IX signal and propeptide domains, Protein S GLA domain, Factor IX EGF1 domain, with Factor VII EGF2 and catalytic domains and an RKRRKR sequence (SEQ ID NO:6) were alive and showed no adverse symptoms approximately five weeks post-injection. Blood is collected once a week from the mice and after six to eight weeks following injection the level of mouse Factor VII polypeptide can be measured. Also, antigen levels to the mouse Factor VII polypeptides can be determined indirectly by measuring the clotting activity in vitro from blood samples of the injected mice (Margaritas et al., *Gene Therapy* 2009; 113:3682-3689).

The foregoing is illustrative of the present invention, and is not to be construed as limiting thereof. The invention is defined by the following claims, with equivalents of the claims to be included therein. All publications, patent applications, patents, patent publications, sequences identified by GenBank® database and/or SNP accession numbers, and other references cited herein are incorporated by reference in their entireties for the teachings relevant to the sentence and/or paragraph in which the reference is presented.

What is claimed is:

1. A method of treating a bleeding disorder in a subject having a bleeding disorder by administering a chimeric Factor VIIa polypeptide, wherein the chimeric Factor VIIa polypeptide comprises EGF-2 and catalytic domains of Factor VII; a GLA domain selected from the group consisting of the GLA domain of Factor IX and the GLA domain of protein S; and an EGF-1 domain of Factor IX.

2. The method of claim 1, wherein the bleeding disorder is selected from the group consisting of: clotting factor deficiencies; defective platelet function; thrombocytopenia; von Willebrand's disease; inhibition of clotting factors; bleeding induced by surgery; and, bleeding induced by trauma.

3. The method of claim 2, wherein the bleeding disorder is a clotting factor deficiency.

4. The method of claim 3, wherein the clotting factor deficiency is hemophilia.

5. The method of claim 1, wherein treating the bleeding disorder comprises administering to the subject a nucleic acid molecule comprising a nucleotide sequence encoding the chimeric Factor VIIa polypeptide.

6. The method of claim 1, wherein the GLA domain is a GLA domain of Factor IX and the EGF-1 domain is an EGF-1 domain of Factor IX.

7. The method of claim 1, wherein the GLA domain is a GLA domain of Protein S and the EGF-1 domain is an EGF-1 domain of Factor IX.

* * * * *